(12) United States Patent
Vecchiotti et al.

(10) Patent No.: US 9,113,989 B2
(45) Date of Patent: Aug. 25, 2015

(54) METHODS AND DEVICES FOR SUPPORTING, ELEVATING, OR COMPRESSING INTERNAL STRUCTURES

(75) Inventors: Richard G. Vecchiotti, San Francisco, CA (US); Venita Chandra, Belmont, CA (US); Ross D. Venook, Burlingame, CA (US); Tatum Tarin, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1688 days.

(21) Appl. No.: 12/191,980

(22) Filed: Aug. 14, 2008

(65) Prior Publication Data

US 2009/0082617 A1    Mar. 26, 2009

Related U.S. Application Data

(60) Provisional application No. 60/964,801, filed on Aug. 14, 2007.

(51) Int. Cl.
*A61F 2/00*    (2006.01)

(52) U.S. Cl.
CPC ........ *A61F 2/0045* (2013.01); *A61F 2250/0003* (2013.01); *A61F 2250/0006* (2013.01); *A61F 2250/0007* (2013.01)

(58) Field of Classification Search
CPC ................. A61F 2/00–2/0054; A61F 2/0063; A61F 2250/0004–2250/0007; A61B 2017/00805; A61B 2018/00523
USPC ........ 600/29–32, 37, 201–246; 128/855, 886, 128/897–899; 606/139–158; 601/19
See application file for complete search history.

(56) References Cited

U.S. PATENT DOCUMENTS

| 4,019,499 A | 4/1977 | Fitzgerald |
| 4,106,511 A | 8/1978 | Erlandsson |
| 4,194,508 A | 3/1980 | Anderson |

(Continued)

FOREIGN PATENT DOCUMENTS

| EP | 0 643 945 A2 | 3/1995 |
| EP | 0 643 945 A3 | 3/1995 |

(Continued)

OTHER PUBLICATIONS

International Search Report mailed on Feb. 23, 2009, for PCT Patent Application No. PCT/US2008/009748, filed on Aug. 14, 2008, seven pages.

(Continued)

*Primary Examiner* — Catherine B Kuhlman
(74) *Attorney, Agent, or Firm* — Stoel Rives LLP

(57) ABSTRACT

The present invention relates generally to dynamic support devices, methods of providing dynamic support to target tissues, and kits comprising these devices. These devices may have particular utility in providing support to the urethra. The dynamic support devices generally comprise at least one attachment member for attachment to bodily tissue, and at least one support member, where the device capable of assuming a first configuration and a second configuration. The dynamic support devices may be configured to support a target tissue when the device is in its second configuration. The support member may comprise one or more rotating components, one or more deformable components, one or more sliding components, or a combination thereof.

1 Claim, 21 Drawing Sheets

(56) References Cited

U.S. PATENT DOCUMENTS

| | | |
|---|---|---|
| 4,248,214 A | 2/1981 | Hannah et al. |
| 4,248,229 A | 2/1981 | Miller |
| 4,428,365 A * | 1/1984 | Hakky .......................... 600/31 |
| 4,705,029 A | 11/1987 | Borodulin et al. |
| 4,739,759 A | 4/1988 | Rexroth et al. |
| 4,760,840 A | 8/1988 | Fournier, Jr. et al. |
| 4,846,817 A | 7/1989 | Mohr et al. |
| 4,911,149 A | 3/1990 | Borodulin et al. |
| 5,030,199 A | 7/1991 | Barwick et al. |
| 5,149,326 A | 9/1992 | Woodgrift et al. |
| 5,193,553 A | 3/1993 | Kalinoski |
| 5,342,374 A | 8/1994 | Wan et al. |
| 5,366,490 A | 11/1994 | Edwards et al. |
| 5,370,675 A | 12/1994 | Edwards et al. |
| 5,507,754 A | 4/1996 | Green et al. |
| 5,514,176 A | 5/1996 | Bosley, Jr. |
| 5,518,504 A | 5/1996 | Polyak |
| 5,542,915 A | 8/1996 | Edwards et al. |
| 5,549,617 A | 8/1996 | Green et al. |
| 5,554,110 A | 9/1996 | Edwards et al. |
| 5,562,598 A | 10/1996 | Whalen et al. |
| 5,562,689 A * | 10/1996 | Green et al. .................. 606/151 |
| 5,593,389 A | 1/1997 | Chang |
| 5,599,294 A | 2/1997 | Edwards et al. |
| 5,652,842 A | 7/1997 | Siegrist, Jr. et al. |
| 5,685,839 A | 11/1997 | Edwards et al. |
| 5,704,893 A | 1/1998 | Timm |
| 5,800,378 A | 9/1998 | Edwards et al. |
| 5,899,909 A | 5/1999 | Claren et al. |
| 5,934,283 A | 8/1999 | Willem et al. |
| 5,934,286 A | 8/1999 | Maginot |
| 5,964,727 A | 10/1999 | Edwards et al. |
| 5,964,806 A | 10/1999 | Cook et al. |
| 5,984,910 A | 11/1999 | Berke |
| 5,993,472 A | 11/1999 | Hermann et al. |
| 6,036,635 A | 3/2000 | Altshuler |
| 6,042,534 A | 3/2000 | Gellman et al. |
| 6,045,498 A | 4/2000 | Burton et al. |
| 6,074,341 A | 6/2000 | Anderson et al. |
| 6,095,969 A | 8/2000 | Karram et al. |
| 6,104,959 A | 8/2000 | Spertell |
| 6,117,067 A | 9/2000 | Gil-Vernet |
| 6,124,461 A | 9/2000 | Shoemaker |
| 6,129,726 A | 10/2000 | Edwards et al. |
| 6,139,544 A | 10/2000 | Mikus et al. |
| 6,159,170 A | 12/2000 | Borodulin et al. |
| 6,190,407 B1 | 2/2001 | Ogle et al. |
| 6,210,419 B1 | 4/2001 | Mayenberger et al. |
| 6,248,101 B1 | 6/2001 | Whitmore, III et al. |
| 6,267,782 B1 | 7/2001 | Ogle et al. |
| 6,273,852 B1 | 8/2001 | Lehe et al. |
| 6,328,687 B1 | 12/2001 | Karram et al. |
| 6,342,049 B1 | 1/2002 | Nichols |
| 6,365,590 B1 | 4/2002 | Shoemaker |
| 6,366,814 B1 | 4/2002 | Boveja et al. |
| 6,382,214 B1 | 5/2002 | Raz et al. |
| 6,406,423 B1 | 6/2002 | Scetbon |
| 6,419,624 B1 | 7/2002 | Burton et al. |
| 6,419,653 B2 | 7/2002 | Edwards et al. |
| 6,419,701 B1 | 7/2002 | Cook et al. |
| 6,478,727 B2 | 11/2002 | Scetbon |
| 6,485,422 B1 | 11/2002 | Mikus et al. |
| 6,491,703 B1 | 12/2002 | Ulmsten |
| 6,500,194 B2 | 12/2002 | Benderev et al. |
| 6,506,190 B1 | 1/2003 | Walshe |
| 6,530,879 B1 | 3/2003 | Adamkiewicz |
| 6,575,897 B1 | 6/2003 | Ory et al. |
| 6,579,224 B1 | 6/2003 | Burton et al. |
| 6,596,010 B1 | 7/2003 | Hermann et al. |
| 6,610,054 B1 | 8/2003 | Edwards et al. |
| 6,612,977 B2 | 9/2003 | Staskin et al. |
| 6,638,211 B2 | 10/2003 | Suslian et al. |
| 6,645,138 B2 | 11/2003 | Cook et al. |
| 6,648,921 B2 | 11/2003 | Anderson et al. |
| 6,684,108 B2 | 1/2004 | Surbeck et al. |
| 6,702,827 B1 | 3/2004 | Lund et al. |
| 6,709,385 B2 | 3/2004 | Forsell |
| 6,786,542 B1 | 9/2004 | Nuzzarello |
| 6,814,712 B1 | 11/2004 | Edwards et al. |
| 6,830,052 B2 | 12/2004 | Carter et al. |
| 6,852,091 B2 | 2/2005 | Edwards et al. |
| 6,879,859 B1 | 4/2005 | Boveja |
| 6,911,002 B2 | 6/2005 | Fierro |
| 6,911,003 B2 | 6/2005 | Anderson et al. |
| 6,953,428 B2 | 10/2005 | Gellman et al. |
| 6,969,380 B1 | 11/2005 | Zunker |
| 6,971,986 B2 | 12/2005 | Staskin et al. |
| 7,014,606 B2 | 3/2006 | Burton et al. |
| 7,037,317 B2 | 5/2006 | Hermann et al. |
| 7,056,288 B2 | 6/2006 | Tracey et al. |
| 7,056,333 B2 | 6/2006 | Walshe |
| 7,083,637 B1 | 8/2006 | Tannhauser |
| 7,087,055 B2 * | 8/2006 | Lim et al. .................... 606/99 |
| 7,128,707 B2 | 10/2006 | Banik |
| 7,163,506 B2 | 1/2007 | Grise |
| 7,204,801 B2 | 4/2007 | Grocela |
| 7,223,228 B2 | 5/2007 | Timm et al. |
| 7,395,822 B1 * | 7/2008 | Burton et al. ................ 128/885 |
| 7,776,061 B2 | 8/2010 | Garner et al. |
| 7,815,562 B2 * | 10/2010 | Chu ................................ 600/30 |
| 7,871,416 B2 | 1/2011 | Phillips |
| 7,981,023 B2 * | 7/2011 | Nowlin et al. .................. 600/30 |
| 2001/0018549 A1 | 8/2001 | Scetbon |
| 2001/0031941 A1 | 10/2001 | Edwards et al. |
| 2002/0028181 A1 | 3/2002 | Miller et al. |
| 2002/0050769 A1 | 5/2002 | Pelrine et al. |
| 2002/0099258 A1 | 7/2002 | Staskin et al. |
| 2002/0099259 A1 | 7/2002 | Anderson et al. |
| 2002/0103518 A1 | 8/2002 | Surbeck et al. |
| 2002/0147382 A1 | 10/2002 | Neisz et al. |
| 2002/0151763 A1 | 10/2002 | Cook et al. |
| 2002/0156342 A1 | 10/2002 | Burton et al. |
| 2002/0165566 A1 | 11/2002 | Ulmsten |
| 2002/0183740 A1 | 12/2002 | Edwards et al. |
| 2002/0188170 A1 | 12/2002 | Santamore et al. |
| 2003/0023144 A1 | 1/2003 | Tracey et al. |
| 2003/0036676 A1 | 2/2003 | Scetbon |
| 2003/0045774 A1 | 3/2003 | Staskin et al. |
| 2003/0062052 A1 | 4/2003 | Carter et al. |
| 2003/0078604 A1 | 4/2003 | Walshe |
| 2003/0152522 A1 | 8/2003 | Miller et al. |
| 2003/0195545 A1 | 10/2003 | Hermann et al. |
| 2003/0199732 A1 | 10/2003 | Suslian et al. |
| 2004/0006353 A1 | 1/2004 | Bosley et al. |
| 2004/0015045 A1 | 1/2004 | Burton et al. |
| 2004/0049408 A1 | 3/2004 | Voss et al. |
| 2004/0068203 A1 | 4/2004 | Gellman et al. |
| 2004/0096422 A1 | 5/2004 | Schwartz et al. |
| 2004/0102770 A1 | 5/2004 | Goble |
| 2004/0143152 A1 | 7/2004 | Grocela |
| 2004/0144394 A1 | 7/2004 | Dauner et al. |
| 2004/0144395 A1 | 7/2004 | Evans et al. |
| 2004/0147886 A1 | 7/2004 | Bonni |
| 2004/0249396 A1 | 12/2004 | Lund et al. |
| 2004/0254625 A1 | 12/2004 | Stephens et al. |
| 2004/0267088 A1 | 12/2004 | Kammerer |
| 2005/0010203 A1 | 1/2005 | Edwards et al. |
| 2005/0027160 A1 | 2/2005 | Siegel et al. |
| 2005/0027161 A1 | 2/2005 | Cook et al. |
| 2005/0038452 A1 | 2/2005 | Chu |
| 2005/0070816 A1 | 3/2005 | Coats |
| 2005/0101834 A1 | 5/2005 | Merade |
| 2005/0131274 A1 | 6/2005 | Suslian et al. |
| 2005/0171583 A1 | 8/2005 | Mosher et al. |
| 2005/0203344 A1 * | 9/2005 | Orban et al. .................. 600/204 |
| 2005/0222559 A1 | 10/2005 | Shiono et al. |
| 2005/0234291 A1 * | 10/2005 | Gingras ......................... 600/30 |
| 2005/0245787 A1 | 11/2005 | Cox et al. |
| 2005/0250978 A1 | 11/2005 | Kammerer |
| 2005/0256364 A1 | 11/2005 | Burton et al. |
| 2005/0261547 A1 | 11/2005 | Bouffier |
| 2005/0277806 A1 | 12/2005 | Cristalli |
| 2006/0004246 A1 | 1/2006 | Selikowitz |
| 2006/0015001 A1 | 1/2006 | Staskin et al. |

(56) References Cited

U.S. PATENT DOCUMENTS

| | | |
|---|---|---|
| 2006/0041185 A1 | 2/2006 | Browning |
| 2006/0058574 A1 | 3/2006 | Priewe et al. |
| 2006/0058830 A1 | 3/2006 | Hermann et al. |
| 2006/0069301 A1 | 3/2006 | Neisz et al. |
| 2006/0089525 A1 | 4/2006 | Mamo et al. |
| 2006/0112536 A1 | 6/2006 | Herweck et al. |
| 2006/0134168 A1 | 6/2006 | Chappa et al. |
| 2006/0195006 A1 | 8/2006 | Daurelle et al. |
| 2006/0195007 A1 | 8/2006 | Anderson et al. |
| 2006/0199996 A1 | 9/2006 | Caraballo et al. |
| 2006/0235447 A1 | 10/2006 | Walshe |
| 2006/0252980 A1 | 11/2006 | Arnal et al. |
| 2006/0264698 A1 | 11/2006 | Kondonis et al. |
| 2006/0281964 A1 | 12/2006 | Burton et al. |
| 2006/0281966 A1 | 12/2006 | Peacock, III |
| 2006/0287570 A1 | 12/2006 | Whalen et al. |
| 2007/0015957 A1 | 1/2007 | Li |
| 2007/0021649 A1 | 1/2007 | Nowlin et al. |
| 2007/0032695 A1 | 2/2007 | Weiser |
| 2007/0038017 A1* | 2/2007 | Chu .......................... 600/37 |
| 2007/0049790 A1 | 3/2007 | Wagner et al. |
| 2007/0049791 A1 | 3/2007 | Merade et al. |
| 2007/0156012 A1 | 7/2007 | Tracey et al. |
| 2007/0162120 A1 | 7/2007 | Bouffier |
| 2007/0299296 A1* | 12/2007 | Vaska .......................... 600/16 |
| 2008/0004487 A1 | 1/2008 | Haverfield |
| 2008/0009665 A1 | 1/2008 | Merade et al. |
| 2008/0045782 A1 | 2/2008 | Jimenez |
| 2008/0167518 A1* | 7/2008 | Burton et al. ............... 600/31 |
| 2008/0269548 A1* | 10/2008 | Vecchiotti et al. ........... 600/30 |
| 2010/0198000 A1 | 8/2010 | Wagner et al. |
| 2010/0261950 A1* | 10/2010 | Lund et al. .................. 600/30 |
| 2011/0124954 A1* | 5/2011 | Ogdahl et al. ............... 600/30 |

FOREIGN PATENT DOCUMENTS

| | | |
|---|---|---|
| EP | 1 238 638 A1 | 9/2002 |
| WO | WO-01/45589 A1 | 6/2001 |
| WO | WO-02/078552 A1 | 10/2002 |
| WO | WO 2005087154 A2 * | 9/2005 .............. A61F 6/00 |
| WO | WO-2005/122954 A1 | 12/2005 |
| WO | WO-2007/018532 A1 | 2/2007 |
| WO | WO-2007/022065 A2 | 2/2007 |
| WO | WO-2007/022065 A3 | 2/2007 |
| WO | WO-2008/134064 A1 | 11/2008 |
| WO | WO-2009/023256 A2 | 2/2009 |

OTHER PUBLICATIONS

Written Opinion of the International Searching Authority, mailed on Feb. 23, 2009, for PCT Patent Application No. PCT/US2008/009748, filed on Aug. 14, 2008, nine pages.

International Search Report mailed on Aug. 13, 2008, for PCT Application No. PCT/US2008/005488, filed on Apr. 28, 2008, 6 pages.

International Preliminary Report on Patentability mailed on Nov. 12, 2009, for PCT Patent Application No. PCT/US2008/005488, filed on Apr. 28, 2008, 11 pages.

Israeli Office Action for Patent Application No. 1985696, filed on Aug. 14, 2008, 2 pages (English Translation).

Non-Final Office Action mailed on Apr. 13, 2011, for U.S. Appl. No. 12/110,911, filed on Apr. 28, 2008, 14 pages.

Non-Final Office Action mailed on Jan. 12, 2012, for U.S. Appl. No. 12/110,911, filed on Apr. 28, 2008, 14 pages.

Written Opinion mailed on Aug. 13, 2008, for PCT Application No. PCT/US2008/005488, filed on Apr. 28, 2008, 9 pages.

Yamana, T. et al. (Nov. 2004, e-pub. Oct. 11, 2004). "Perineal Puborectalis Sling Operation for Fecal Incontinence: Preliminary Report," *Dis Colon Rectum* 47(11):1983-1989.

\* cited by examiner

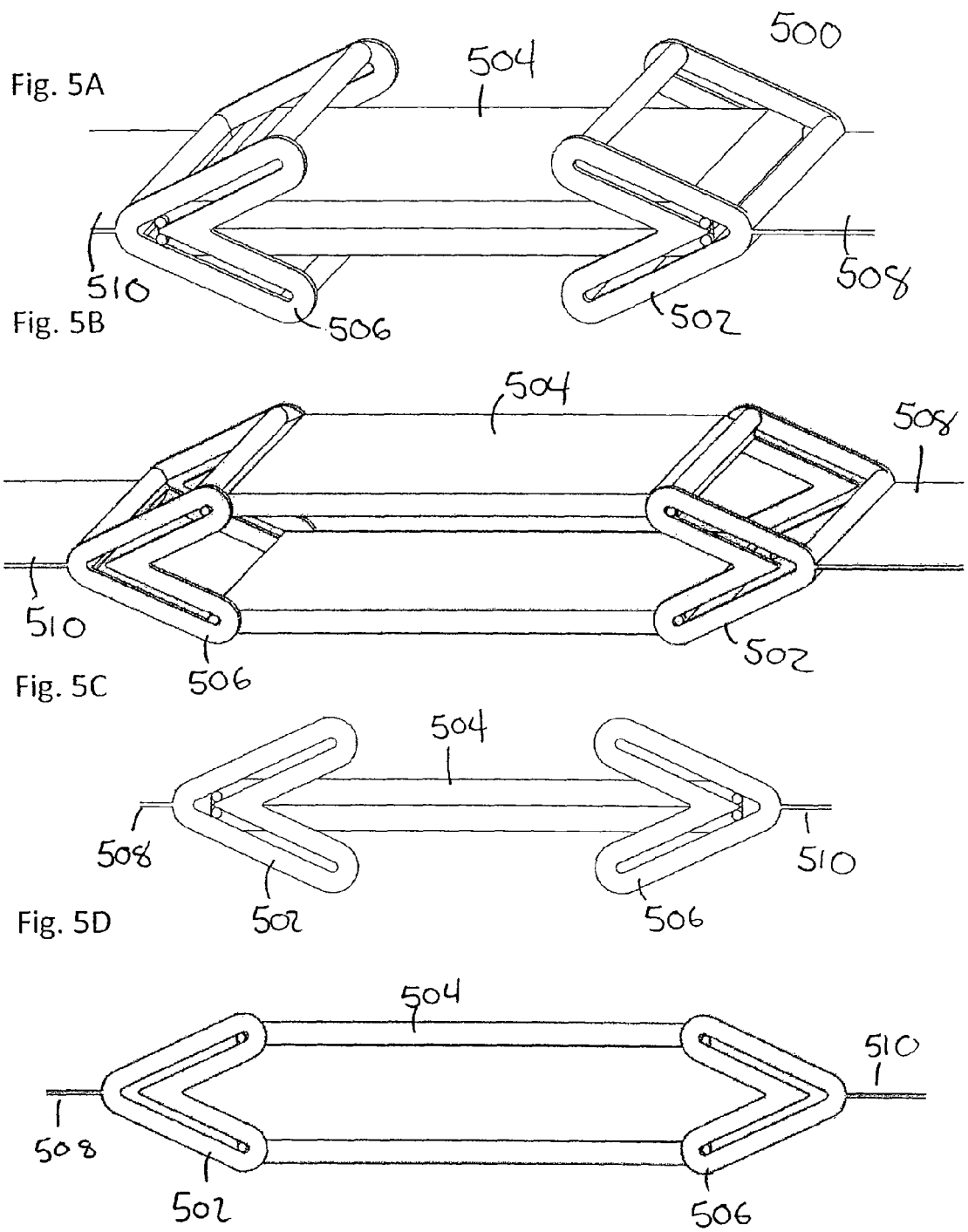

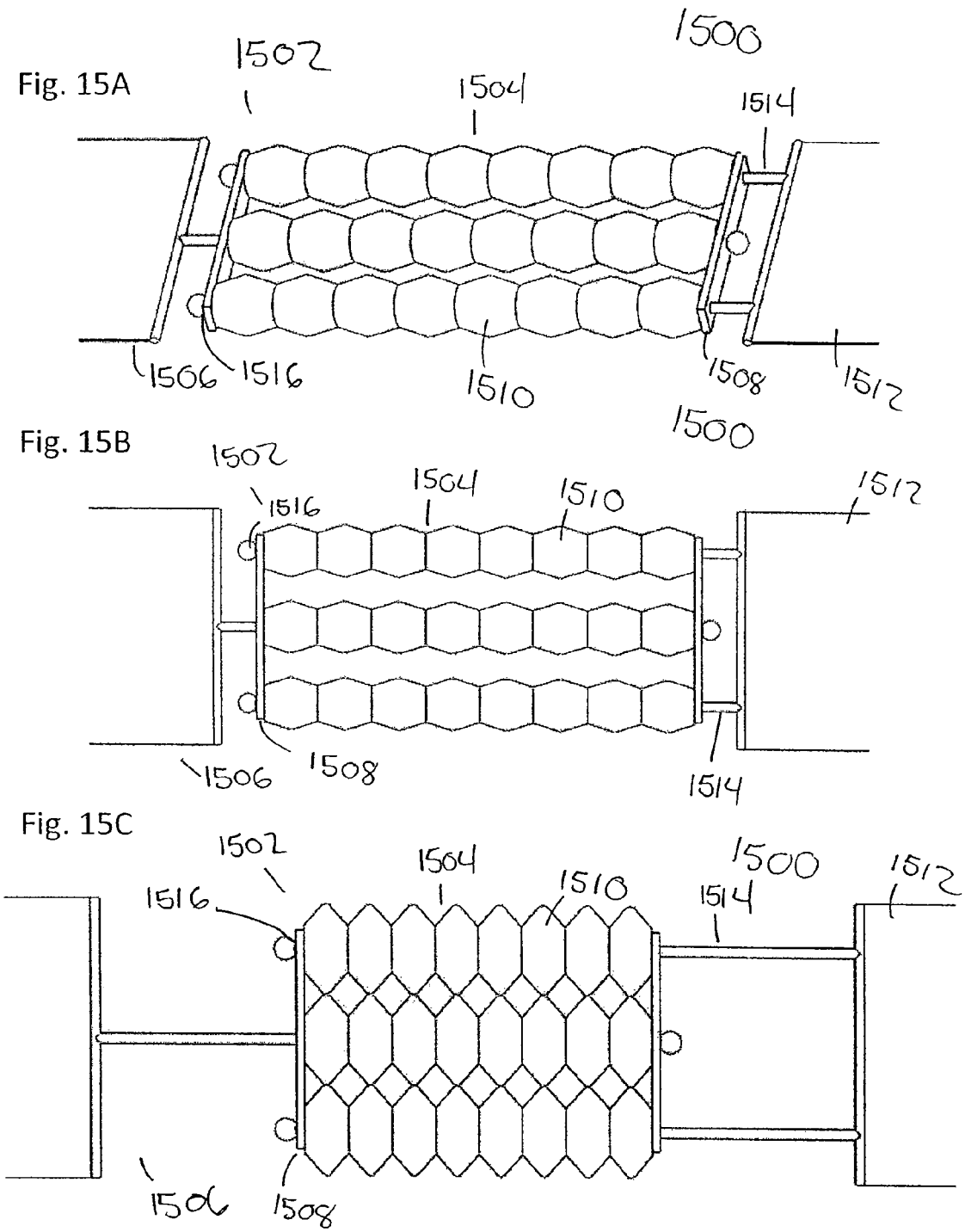

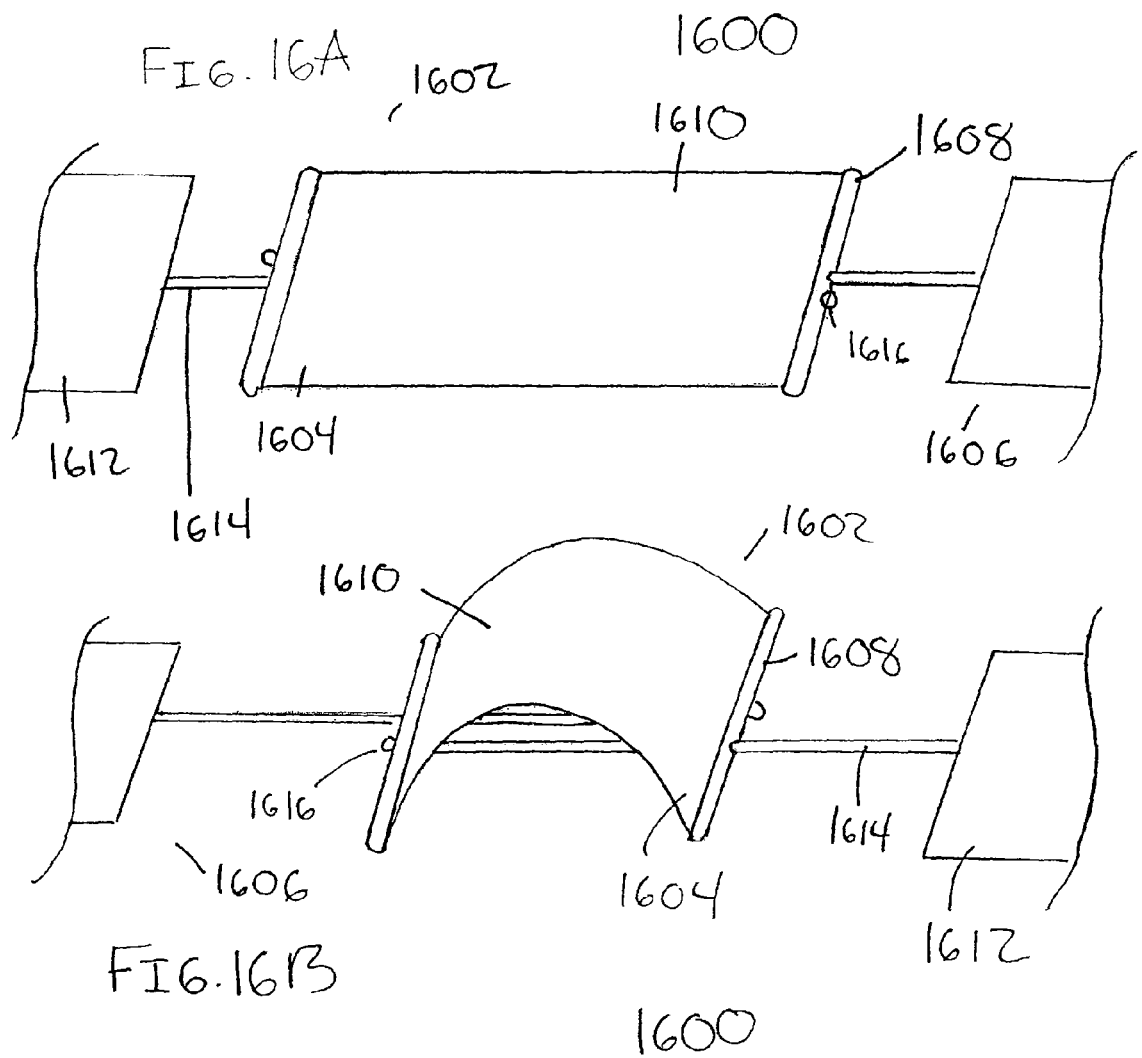

METHODS AND DEVICES FOR SUPPORTING, ELEVATING, OR COMPRESSING INTERNAL STRUCTURES

CROSS-REFERENCE TO RELATED APPLICATIONS

The application claims priority to U.S. Provisional Pat. App. No. 60/964,801 filed Aug. 14, 2007, the entirety of which is hereby incorporated by reference herein.

FIELD

The present invention relates generally to devices that provide dynamic and/or adjustable support to an anatomical location, methods of using them and kits including them. The devices may find particular utility in the area of urinary incontinence.

BACKGROUND OF THE INVENTION

Loss of bladder control, also known as urinary incontinence, is a widespread, debilitating condition, affecting millions worldwide. Associated with symptoms such as sleep deprivation, urosepsis, and skin irritation, urinary incontinence can have significant physiological, psychological, and social impacts on quality of life. The most common form of urinary incontinence, stress urinary incontinence, involves the involuntary leakage of urine upon sneezing, coughing, or other exertion. This leakage generally occurs when an increase in abdominal pressure during a stress event overcomes the body's urinary continence mechanisms.

During urination, muscles in the bladder contract and force urine from the bladder into the urethra. At the same time, the musculature of the urethral wall and the urinary sphincter relax, allowing urine to pass through the urethra and out of the body. During other activity, the urinary sphincter and the musculature of the urethral wall remain contracted, coapting the urethra. The urethra is further supported by a hammock-like pelvic floor which includes endopelvic fascia and, in women, the anterior vaginal wall. Generally, increases in abdominal pressure (generated, for example, by stress events such as coughing or exertion) push the urethra against the pelvic floor, further coapting the urethra.

Stress urinary incontinence is thought to occur by one, or both, of two mechanisms. The first mechanism results from failure of the urinary sphincter and musculature of the urethral wall. In this mechanism, called intrinsic sphincter deficiency, the urethral sphincter muscles are unable to adequately constrict the urethra, which results in urine loss during stress events. Intrinsic sphincter deficiency may result from operative trauma, scarring, denervation or atrophy. The second mechanism, urethral hypermobility, occurs when support structures within the pelvic floor become weakened or damaged. In these cases, the pelvic floor no longer properly functions to compress the urethra upon increases in abdominal pressure.

Fecal incontinence results from a loss of bowel control and an inability to hold stool within the body. During defecation, muscles in the rectum contract and force stool through the anus. Simultaneously, sphincters of the anus relax, thereby allowing stool to pass out of the body. During other activity, the anal sphincters remain contracted, preventing passage of stool therethrough.

Fecal incontinence is thought to be caused by one, or more, of a number of mechanisms. Constipation can result in the stretching and eventual weakening of the rectal muscles, which makes the rectum unable to adequately contain stool. Similarly, physical damage to the internal or external anal sphincters may result in a similar effect. In some situations, nerve damage resulting from childbirth, a stroke or physical injury may prevent the anal sphincters from functioning properly.

Given the widespread and debilitating nature of urinary and fecal incontinence, additional devices for treating urinary and fecal incontinence would be desirable. In particular, adjustable devices, which may allow physicians to change, following or during implantation, the amount of support a device provides would be desirable. Devices that dynamically provide different levels of support during times of stress would also be desirable.

BRIEF SUMMARY OF THE INVENTION

Described here are dynamic support devices, methods of using them, and kits that may incorporate them. The devices may be useful in a variety of locations within the body, for a number of different functions. In some of the devices described here, the devices have first and second attachment members and at least one support member positioned therebetween, where the support member has a first configuration and a second configuration. In some variations, the at least one support member may comprise one or more sliding members. The one or more sliding member may be one or more shaped plates, one or more housing components, or one or more tracks. In some variations, the at least one support member comprises one or more platforms or grooves. In other variations, the support member comprises an internal component that may be at least partially housed within the sliding members, and may change shape when the support member is in its second configuration. In some variations, the sliding member may slide from a first position to a second position upon application of a first force to one or more of the first and second attachment members. In some variations, this may change the at least one support member from its first configuration to its second configuration. The at least one support member may be configured to apply a compressive force to a target tissue when the at least one support member is in its second configuration.

Generally, the support members described here may be made of any suitable or useful material. In some variations, for example, the support member comprises a shape memory material. In other variations, the support member comprises a stimulus responsive material. In still other variations, the support member comprises a deformable material. In some variations, the support member comprises a mesh. Of course, the support member may comprise some combination of these, or other, materials.

The attachment members described here may be made of any suitable or useful materials. In some variations, for example, one or more of the attachment members may comprise one or more tissues or synthetic materials. In other variations, one or more of the attachment members may comprise polypropylene. In some variations, one or more of the attachment members may comprise a mesh. Of course, the attachment members may comprise some combination of these or other materials.

Similarly, the attachment members described here may have any shape or configuration of elements. For example, the first and second attachment members may be approximately rectangular. Additionally, these members may be of any suitable size, for example, between about 1 and about 4 cm in width and between about 5 and about 20 cm in length. Furthermore, one or more of the attachment members may promote tissue ingrowth. In some variations, one or more of the attachment members may comprise an anchoring component. In some of these variations, one or more of the attachment members may comprise at least one connection member for connecting the anchoring component to the support member.

In some variations, the support devices described here comprise first and second attachment members and at least one support member positioned therebetween, where the device has a first configuration and a second configuration, and where the at least one support member is configured to rotate around an axis of rotation upon application of a first force to one or more of the first and second attachment members, thereby changing the device from its first configuration to its second configuration. In some variations, the at least one support member is configured to apply a compressive force to the tissue when the device is in its second configuration. In some of these variations, the direction of the compressive force may be substantially parallel to the axis of rotation. In some variations, support member is threaded. In other variations, the support member is non-expandable.

In other variations of the devices described here, the devices comprise first and second attachment members and at least one support member positioned therebetween, where the device has a first configuration and a second configuration and wherein the at least one support member comprises two or more sections that are configured to rotate around a single pivot point, thereby changing the device from the first configuration to the second configuration. In some variations, the two or more sections may compress a target tissue when the device is in its second configuration.

In still other variations, the devices comprise first and second attachment members and at least one support member positioned therebetween, where the at least one support member comprises at least one deformable component, where the at least one support member has a first and a second configuration and where the device is configured to compress the at least one deformable component upon application of a first force to one or more of the first and second attachment members, thereby changing the at least one support member from its first configuration to its second configuration. In some variations the support member is configured to apply a compressive force to the tissue when the at least one support member is in its second configuration. In some variations, the deformable component comprises an elastomeric material. In other variations, the deformable component is semi-rigid.

In other variations of the devices described here, the device comprises a sling that comprises one or more attachment portions and at least one supporting bladder positioned therebetween, one or more lateral bladders positioned on the one or more attachment portions and in fluid communication with the at least one supporting bladder. In some variations, the device is configured to transfer a fluid from the one or more lateral bladders to the at least one supporting bladder upon application of a first force to the one or more attachment portions. In other variations, the at least one supporting bladder is configured to apply a force to a target tissue when a fluid is in the at least one supporting bladder.

In yet other variations, the devices described here comprise first and second attachment members and a first plurality of rotating arms positioned therebetween, where the first plurality of rotating arms are configured to rotate in the same direction relative to a first plane upon application of a first force to one or more of the first and second attachment members. In some variations, the devices further comprises a second plurality of rotating arms configured to rotate in the same direction relative to a second plane upon application of a first force to one or more of the first and second attachment members. In other variations, the device further comprises one or more platforms.

Methods of supporting tissues are also described here. In general, the methods comprise implanting a device into a patient to support a target tissue. In some methods, the device may be any of the support devices described here. In some of these methods, the support member is placed underneath the target tissue.

In some methods, implanting the device comprises attaching one or more of the attachment members to soft tissues. In other methods, implanting the device comprises attaching one or more of the attachment members to bony structures (e.g., pelvic bony structures). The device may be implanted by any number of approaches. The device may be implanted, for example, using a transvaginal approach, using a transperineal approach, and the like.

In some variations, implanting the device comprises passing the first attachment member through a first obturator foramen and passing the second attachment member through a second obturator foramen. In other variations, implanting the device comprises securing an end of the first attachment member in tissue within or external to a first obturator foramen and securing an end of the second attachment member in tissue within or external to a second obturator foramen.

In some variations, implanting the device comprises positioning the device such that at least a portion of each of the first and second attachment members are located in the retropubic space. In other variations, implanting the device comprises positioning the device such that at least a portion of each of the first and second attachment members are located in the prepubic space. In some of the methods described here, the devices comprise at least one attachment member and at least one support member connected thereto, where the support member has a first configuration and a second configuration. In some methods, the support member is configured to provide support to a target tissue when the support member is in its second configuration. In some of these methods, the target tissue is urethral tissue. In others of these methods, the tissue is rectal tissue. Any of the devices described here may be implanted in any of the ways as described above.

BRIEF DESCRIPTION OF THE DRAWINGS

FIG. 1A is a side view of the female pelvic anatomy. FIG. 1B is a side view of the male pelvic anatomy. FIGS. 1C & 1D are transverse cross-sections of the female pelvic anatomy.

FIGS. 5A and 5B are perspective views of a variation of a support member having sliding members. FIG. 5C and FIG. 5D are side views of the support member shown in FIGS. 5A and 5B.

FIG. 15A is a perspective view of one variation of a support device having bellows. FIGS. 15B and 15C are top views of the support device shown in FIG. 15A.

FIGS. 16A and 16B are perspective views of one variation of a support device having a deformable sheet.

DETAILED DESCRIPTION OF THE INVENTION

Described here are devices and methods for providing dynamic support to a target tissue, as well as kits that may include these devices. In some variations, the support devices provide dynamic support to an anatomical location. When reference is made to the term "support" herein, it should be understood that such support can include, without limitation, actions such as holding, compressing, coapting, moving, relocating, and any combinations of the foregoing, and the like. In other variations, the support devices provide dynamic or static support to an anatomical location that can be adjusted during or after implantation. These devices may be useful in providing support to any number of tissues, but may have particular utility in providing support to the urethra or the tissue surrounding the anus. Thus it may be helpful to briefly describe the anatomy of the pelvic region.

Figure 1A:
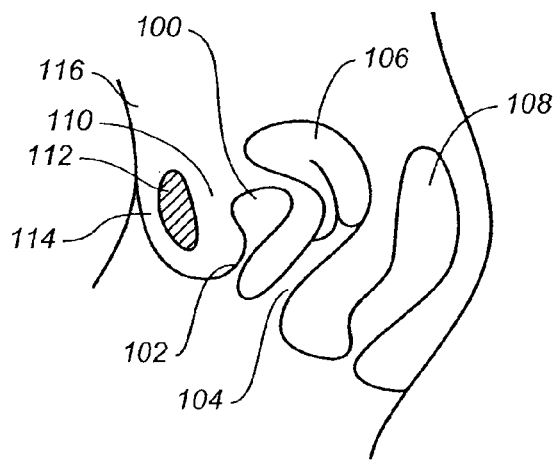
FIGS. 1A-1D are simplified depictions of the pelvic anatomy.
Figure 1B:
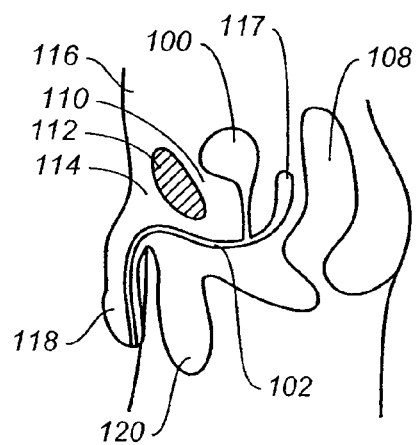
Figure 1C:
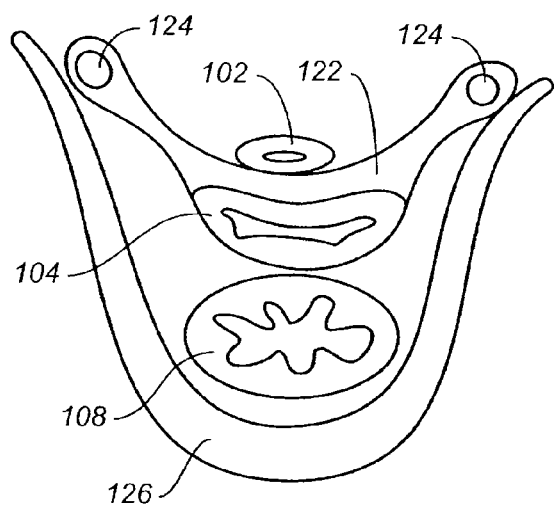
Figure 1D:
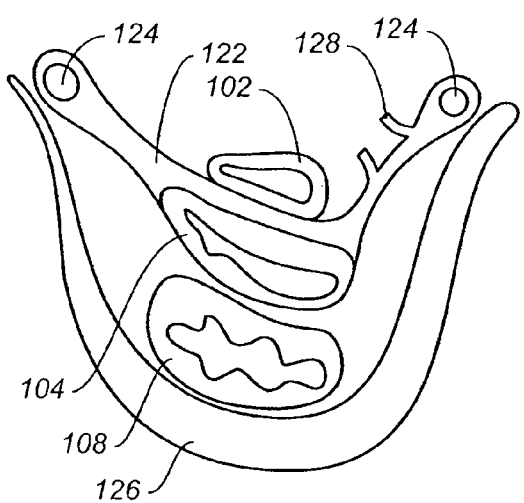

FIGS. 1A-1D provide simplified depictions of the anatomy of the pelvic region. FIG. 1A shows a side view of the female pelvic anatomy. Shown there is bladder (100), urethra (102), vagina (104), uterus (106), rectum (108), retropubic space (110), pubic symphysis (112), prepubic space (114), and rectus fascia (116). FIG. 1B shows a side view of the male pelvic anatomy. Shown there is bladder (100), urethra (102), seminal vesicle (117), rectum (108), retropubic space (110), pubic symphysis (112), prepubic space (114), rectus fascia (116), penis (118) and testes (120). FIG. 1C shows a transverse cross section of the female pelvic anatomy, including urethra (102), vagina (104) and rectum (108). Additionally shown there is endopelvic fascia (122) connecting the vagina (104) to arcus tendineus fasciae pelvis (124), and pubococcygeus muscle (126). FIG. 1D shows a transverse cross section of the female pelvic anatomy of a patient suffering from urethral hypermobility caused by torn ligament (128) in the endopelvic fascia (122).

Some variations of the devices described here are devices that provide dynamic support to a target tissue. Generally, these devices comprise at least one attachment member for attachment to a bodily tissue. These devices also typically comprise one or more support members. Generally, a support member has a first configuration and a second configuration. In some variations, one or more of the one or more support members may apply a force to a target bodily tissue when the one or more support members are in their second configuration.

Figure 2A:
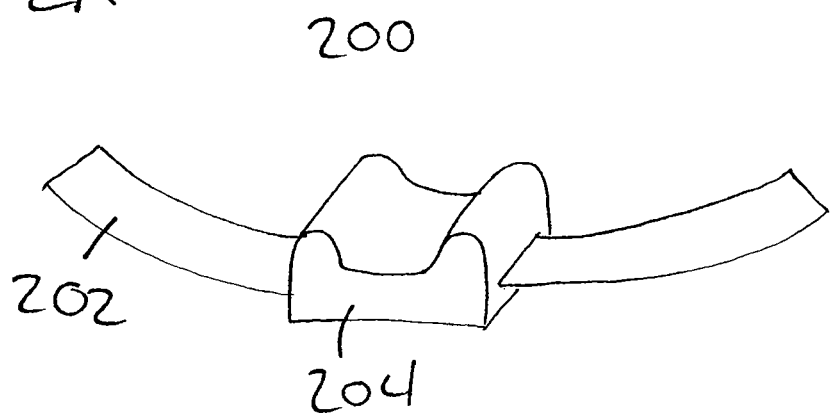
FIGS. 2A and 2B are perspective views of one variation of a dynamic support device including attachment members and a support member.
Figure 2B:
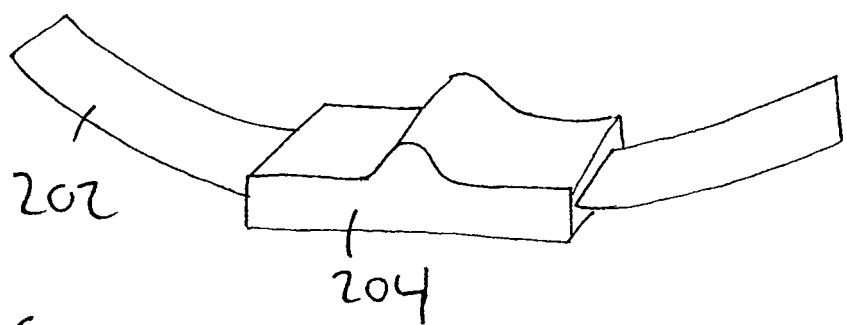
Figure 2C:
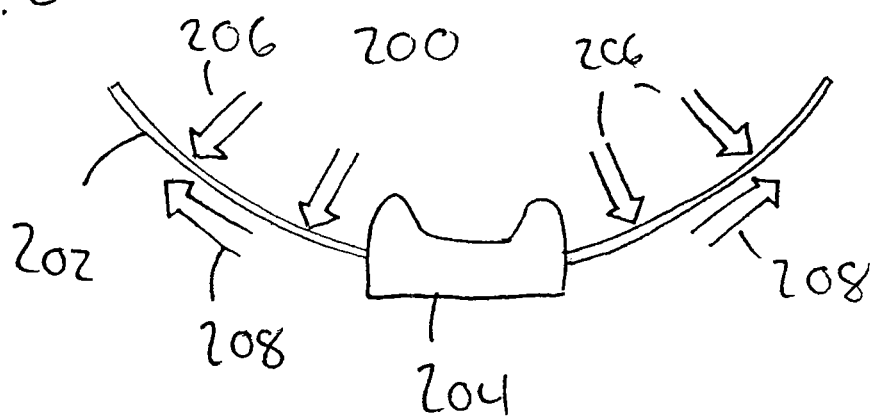
FIG. 2C is a side view of the same dynamic support device.

FIGS. 2A-2C illustrate one variation of a dynamic support device (200), including attachment members (202) and support member (204). Generally, the support member (204) changes from a first configuration, as shown in FIG. 2A, to a second support configuration, as shown in FIG. 2B, upon the application of a force to one or more of the attachment members (202). In other variations, the support member (204) may change between its first and second support configurations upon application of a stimulus to the support member (204).

Generally, the support device (200) has at least one attachment member (202) and at least one support member (204). In some variations, the support device (200) may have two or more attachment members (202), or may have two or more support members (204). The attachment members (202) may be integrally formed with the support members (204), or may be separate components attached to the support members (204). In some variations, additional components, such as a force sensor (not shown), may be positioned between the attachment members (202) and the support members (204), or between the support members (204).

In some variations, the attachment members (202) are attached to bodily tissues during or after implantation of the device (200). After implantation, bodily tissues may apply forces to the attachment members (202). For example, when the device (200) is implanted within the pelvic anatomy, downward movement of the pelvic tissues due to increases in abdominal pressure during a stress event may place an initial force (206) on the attachment members (202). This initial force (206) may then cause a tensile force (208) in the attachment members (202), as illustrated in FIG. 2C. This tensile force (208) may, for example, be substantially normal to the initial force (206). Additionally, this tensile force (208) may be applied to the support member (204), which may cause the support member (204) to move from its first configuration to its second support configuration.

Attachment members may take on any suitable configuration. In some variations, the attachment members are able to translate a first force applied thereto into a second force. In other variations, the attachment members are able to translate a force applied thereto into a stimulus. For example, the attachment member may comprise a piezoelectric material that creates a voltage when a force places the attachment member under stress. In some variations, the attachment members are flexible, or contain flexible components.

Figure 3A:
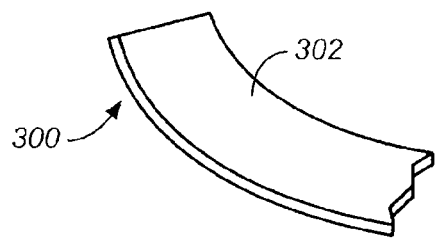
FIGS. 3A-3G are depictions of variations of attachment members.

Any of the attachment members described here may have one or more additional components or members, e.g., anchoring components, connecting members, etc. Illustrative examples of suitable attachment members are shown in FIGS. 3A-3G. In some variations, as shown in FIG. 3A, an attachment member (300) comprises a strip of material (302) without a separate or distinct anchoring component. Material (302) may be made of any suitable biocompatible material. Examples of suitable materials include, but are not limited to, polypropylene, polyethylene, polyester, polycarbonate, polyetheretherketone, polyurethane, polyvinyl chloride, polyethylene terephthalate and silicone. In some variations, material (302) comprises a mesh. In other variations, material (302) includes autologous tissue, homologous tissue, cadaveric tissue, xenograft tissue, collagen matrix materials, synthetic materials, or a combination thereof. In still other variations, material (302) is a bioabsorbable material. While shown in FIG. 3A as generally rectangular, attachment member (300) may have any suitable shape or geometry (e.g., generally circular, generally square, generally elliptical, etc.). In some variations, attachment member (300) may be between about 1 cm and about 4 cm in width, and between about 5 cm and about 20 cm in length.

The attachment member (300) may be configured to promote tissue ingrowth. For example, attachment member (300) may contain ridges, rough edges or other protrusions attached thereto, formed therefrom or formed thereupon for promoting tissue ingrowth. In some variations, attachment member (300) may comprise scar-promoting materials, adhesion promoting materials, or a combination thereof. Attachment member (300) may also be coated or impregnated with a chemical or material that promotes tissue ingrowth. In variations in which the attachment member (300) comprises or includes a mesh, the mesh may have frayed edges or may have protruding edge threads incorporated into the mesh itself. In other variations where the attachment member comprises or includes a mesh, abrasive materials may be woven into the mesh to encourage scarring. In still other variations, the mesh may have pores of a size large enough to allow for tissue ingrowth through the pores.

Figure 3B:
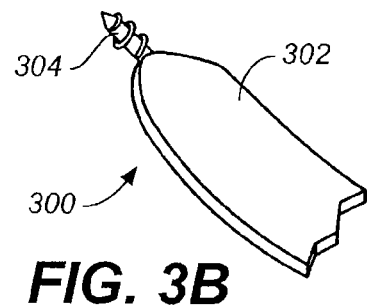
Figure 3C:
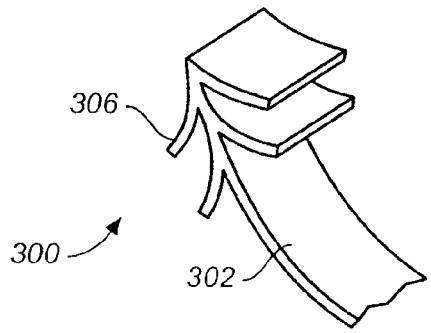

The attachment member (300) may also have one or more integral or separate structures or anchoring components to help anchor or secure it to either soft or bony tissues. In some variations, as shown in FIG. 3B, attachment member (300) comprises a bone screw (304), which may be attached to material (302) as shown there. In other variations, an anchoring component may comprise a hook, clip, staple, or barb, or other anchoring feature. In still other variations, as shown in FIG. 3C, for example, anchoring component (306) may include flaring flaps or a barbed like protrusion. While shown in FIG. 3C as being integral with material (302), flaring flaps (306) may be made distinct from material (302), and may be made from distinct material. The flaring flaps (306) may allow the attachment member (300) to move freely in one direction while resisting movement in the opposite direction, and may allow for the implantation of a support device without making skin incisions, as described below. In other variations, prongs or hooks may be attached to or formed upon an anchoring component. These structures may also allow the attachment member (300) to move freely in one direction while resisting movement in the opposite direction.

Figure 3D:
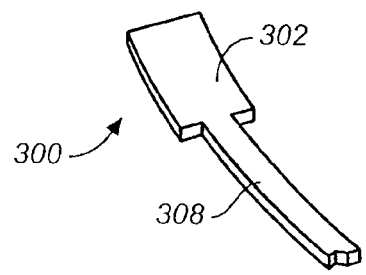
Figure 3E:
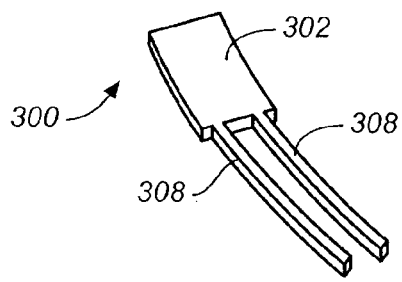
Figure 3F:
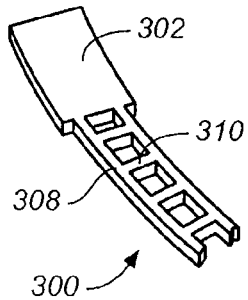
Figure 3G:
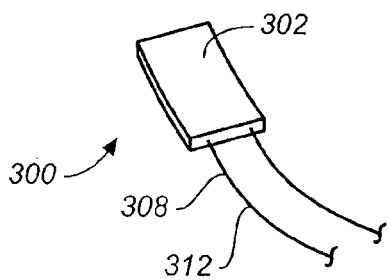

The attachment member (300) may also include one or more connection members (308) for attaching various features or components of the attachment member (300) to the support member, as shown for example, in FIG. 3D. While shown in FIG. 3D as having one connection member (308), attachment member (300) may contain any number of connection members (308). Also it should be understood that the connection member (308) may be made from the same or different material (302) as the rest of the attachment member (300). For example, as illustrated in FIG. 3E, attachment member (300) may comprise two connection members (308). In variations with two or more connection members (308), the attachment member (300) may additionally include links (310) spanning the connection members (308), as shown in FIG. 3F. Connection members (308) and links (310) may be made of any suitable biocompatible material or combination of materials as described above. It should also be understood that while shown in FIG. 3D as being substantially flat and rectangular, connection member (308) need not be. Indeed, connection members (308) may take on any shape or geometry, including, but not limited to, cylindrical, circular, elliptical, cubical, etc. In some variations, as shown in FIG. 3G, connection members (308) may comprise sutures (312) or similar such material.

Again, it is important to note that while certain variations of attachment members have been described just above as having one or more anchoring components or one or more connection members, the attachment members described here need not have any such features. Indeed, in some variations of the devices described here, the attachment member simply comprises a strip or piece of material, as depicted in FIG. 3A, for example. Of course, it should be understood that this material may be of any length, thickness, and size, and in some instances approximates the connection members just described.

Generally, the support member may be any structure capable of assuming a first configuration and a second configuration. The support member generally changes between its configurations upon the application of a force to the support member. In some variations, however, the support member changes between its configurations upon the application of a stimulus to the support member. In some variations, the support member may comprise one or more sliding members that may slide from a first position to a second position, thereby changing the configuration of the device. In other variations, the support member may rotate upon application of a force or stimulus to the support member. In still other variations, the support member may comprise at least one deformable component. In yet other variations, the support member comprises a support bladder and one or more lateral bladders.

In some variations, one or more attachment members may apply a force to the support member, and this force may cause the support member to change between its first and second configurations. In some of these variations, this force may be a tensile force. In other variations, this force may be a compressive force. In other variations, the application of a stimulus to the support member causes the support member to change between its first and second configurations. In some of these variations, one or more of the attachment members may provide the stimulus. In other variations, the stimulus is not provided by the attachment members. In some variations, the support member naturally returns to its first configuration when a force or stimulus is no longer applied to it. In other variations, the support device comprises one or more components that may act to return the support device to its first configuration. In other variations, a different force or stimulus may be applied to support member to return to its original configuration. In some of these variations, this force or stimulus may be provided by the external environment surrounding the support device.

Figure 4A:
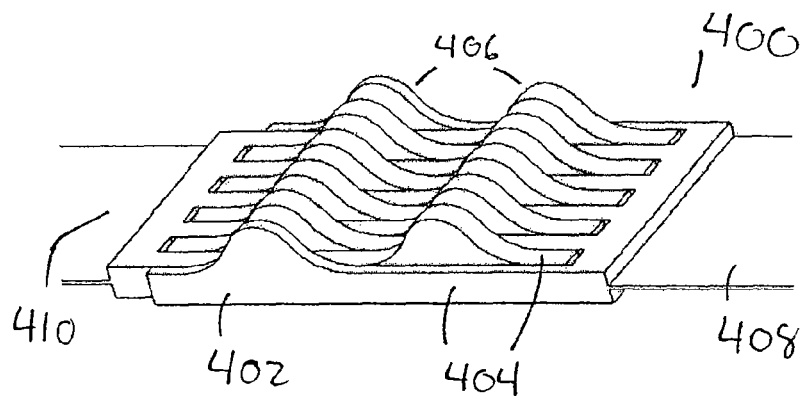
FIGS. 4A-4G are different views of a variation of a support member having sliding members.
Figure 4B:
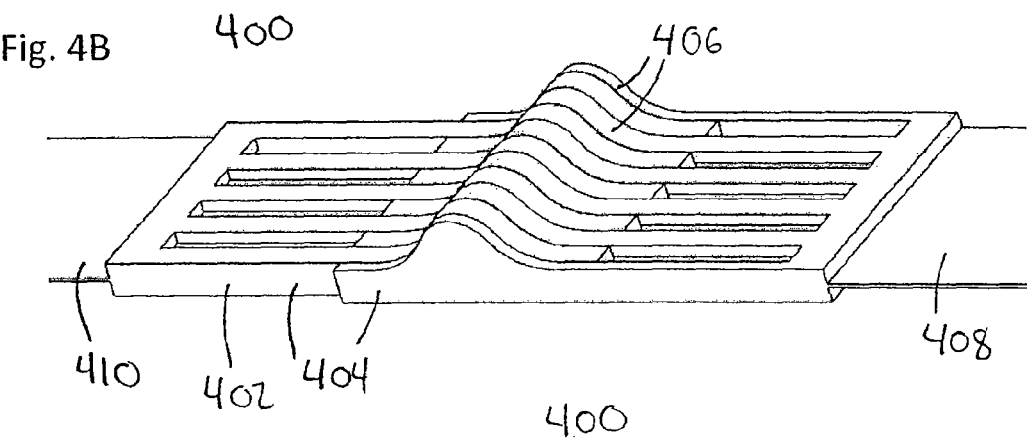

In some variations, the support member comprises one or more sliding members. Generally, application of a force to one or more of the attachment member causes the sliding members to slide between a first position and a second position. In these variations, the movement of the sliding members may change the support member from a first configuration to a second configuration. In some of these variations, the support member may apply a force to a target tissue when the support member is in its second configuration FIGS. 4A-4G show one variation of support member (400) comprising sliding members (402). Shown in FIG. 4A is a perspective view of support member (400) in a first configuration, comprising sliding members (402) which include at least one shaped plate (404), each having an elevated section (406). Also shown there are attachment members (408). While shown in FIGS. 4A-4G as having strips of material (410), attachment members (408) may have any configuration of elements as described above. FIG. 4B shows a perspective view of support member (400) in its second configuration.

Figure 4C:
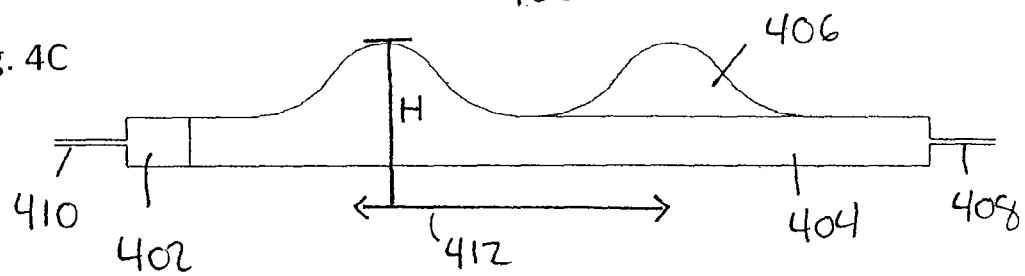
Figure 4D:
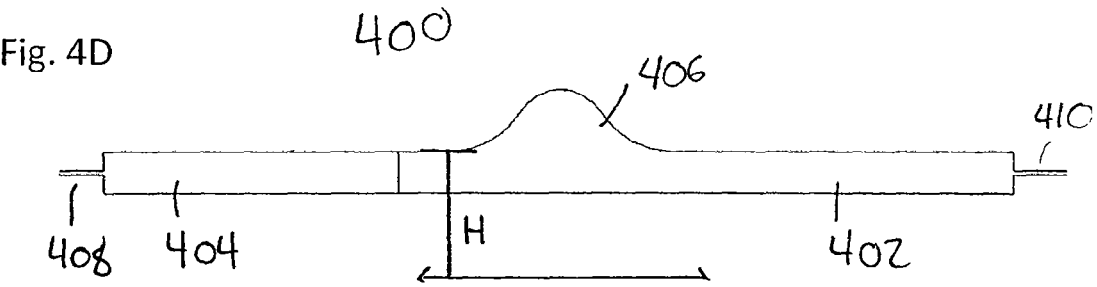
Figure 4E:
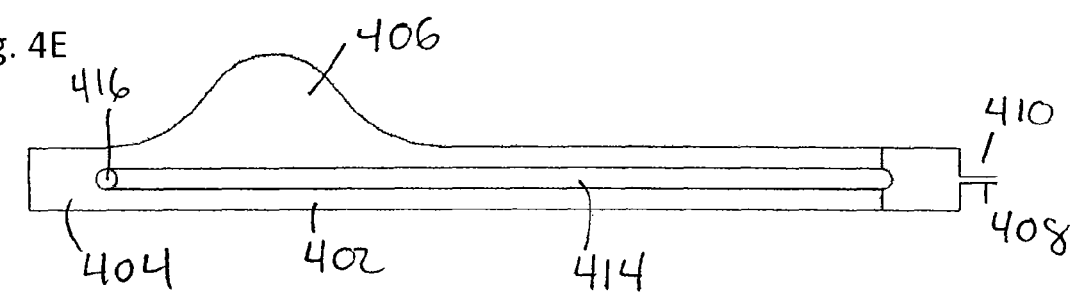
Figure 4F:
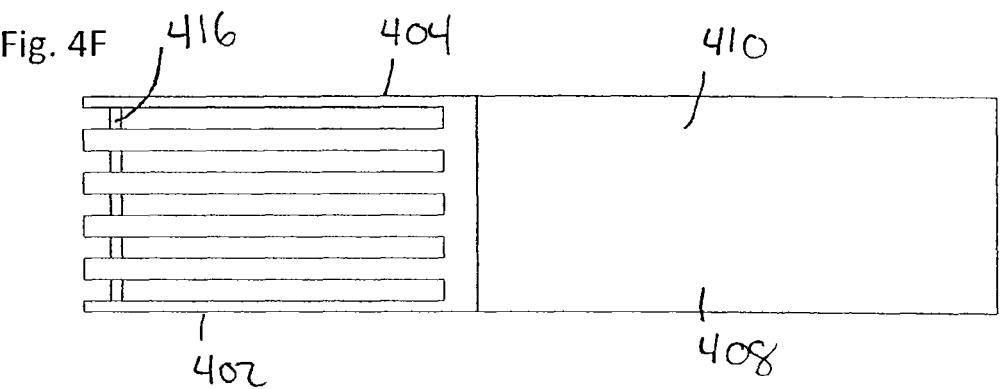

Generally, shaped plates (404) may slide from a first position to a second position when a force is applied to one or more of the attachment members (408). FIG. 4C shows a side view of support member (400) with shaped plates (404) in a first position. When a force is applied to one or more of the attachment members, the shaped plates (404) may slide to a second position, as shown in FIG. 4D. This movement of the shaped plates (404) may change the overall size and/or shape of support member (400), thereby changing support member (400) from a first configuration to a second configuration. For example, in the variation shown in FIGS. 4A-4G, when the shaped plates (404) move between their first and second positions, the overall length of support member (400) increases and the elevated sections (406) move toward the center of the device. Moving an elevated section (406) beneath a target tissue may apply a force to that tissue. Thus, moving elevated sections (406) toward the center of the support member (400) may support a target tissue located thereabove.

Generally, the size and shape of the shaped plates (404) may determine the amount of support that is provided by the support member (400) at a given location. At each point along its length, the top surface of the shaped plates (404) may have a given height (H) relative to a horizontal plane (412). As the height (H) of the shaped plate (404) increases, so may the amount of support provided by the top surface of the shaped plate (404). Thus, the profile of the shaped plate may be configured to provide certain levels of support to a given tissue as the shaped plates move from a first position to a second position. This may be achieved by altering the height (H) of shaped plate (404). For example, in some variations the height (H) of the shaped plate (404) may vary following a linear profile. Such a linear profile may result in a linear change in support provided to a target location as the support device changes between first and second configurations. Similarly, the shaped plates may have heights that vary based on an exponential profile, or an irregular profile.

Similarly, shaped plates (404) may have any size, shape, or configuration. While shown in FIGS. 4A-4G as being substantially rectangular, shaped plates (404) may be any suitable shape profile such as an oval, circle, triangle, diamond, polygon, or the like. Furthermore, shaped plates (404) may have any suitable cross-sectional shape. Additionally, while shown in FIGS. 4A-4G as having one or more elevated sections (406), shaped plates (404) need not. In variations that do include elevated sections (406), these elevated sections (406) may have any size, shape, or configuration. Additionally, each shaped plate (404) may have any number of elevated sections (406) along its profile or cross-section. In other variations, shaped plates (404) may include one or more recessed sections (not shown) along their profile or cross-section that may decrease the amount of support provided to a given area. Recessed sections may have any size, shape, or configuration. In still other variations, a shaped plate (404) may have both elevated sections and recessed sections along its profile or cross-section.

In some variations, the shaped plates (404) may be slidably engagable with one or more portions of the support device. In some variations, one or more shaped plates (404) may be slidably engagable with one or more shaped plates (404), one or more attachment member (404), one or more holding component, as will be described in more detail below, or a combination thereof. Furthermore, shaped plate (404) may be slidably engagable in a number of different ways. In some variations, at least a portion of a shaped plate (404) may fit within a groove or a channel in a holding component or similar structure. In other variations, a shaped plate (404) may comprise one or more grooves (414), as shown in a side view in FIG. 4E. In these variations, a bar (416), pin, or similar structure may be placed through the groove or slot, which may allow the shaped plate (404) to slide relative to the bar. Additionally, the ends of the bar (416) may be attached to one or more attachment members, other shaped plates, holding structure or other component. This may prevent a shaped plate (404) from disengaging from the bar (416). For example, in variations in which the support member (400) includes a plurality of shaped plates (404) disposed in parallel, a bar (416) may be attached to the outermost shaped plates (404) and may pass through grooves defined by some or all of the remaining shaped plates (404), as shown in a top view in FIG. 4F.

Support member (400) may include any number of shaped plates (404). Indeed, support member (400) may include one, two, or three or more shaped plates (404). In variations that include two or more shaped plates (404), shaped plates (404) may have the same size, shape, and configuration, or may have different sizes, shapes, and configurations. In some of these variations, one or more shaped plate (404) may be slidably engaged with one or more other shaped plates (404). Alternatively, one or more shaped plate (404) may be rigidly attached to one or more other shaped plates (404). In still other variations, such as the variations shown in FIGS. 4A-4G, each shaped plates (404) may be both rigidly attached to one or more shaped plates and slidably engaged with one or more plates.

The support member may include or comprise a cover (not shown), but need not. The cover may serve to protect certain components in or of the support member from interference from bodily fluids and tissue ingrowth, while still allowing the support member to change from its first to its second configurations. In other variations, the cover may serve to provide a cushion between part or all of the support member and surrounding tissue. The cover may be made from any suitable biocompatible material. Examples of suitable materials include, but are not limited to, silicone. In some variations, the cover loosely envelops the support member. In other variations, the cover may be fixed to a portion of the support member.

In some variations, the cover envelops the entire support member, but this need not be the case. Indeed, the cover may surround only a portion of the support member. Similarly, multiple covers may surround different portions of the support member. In still other variations, the cover may comprise one or more platforms. These platforms may be made from one or more flexible or rigid materials, and may provide support to a target tissue when the support member is in its second configuration.

Figure 4G:
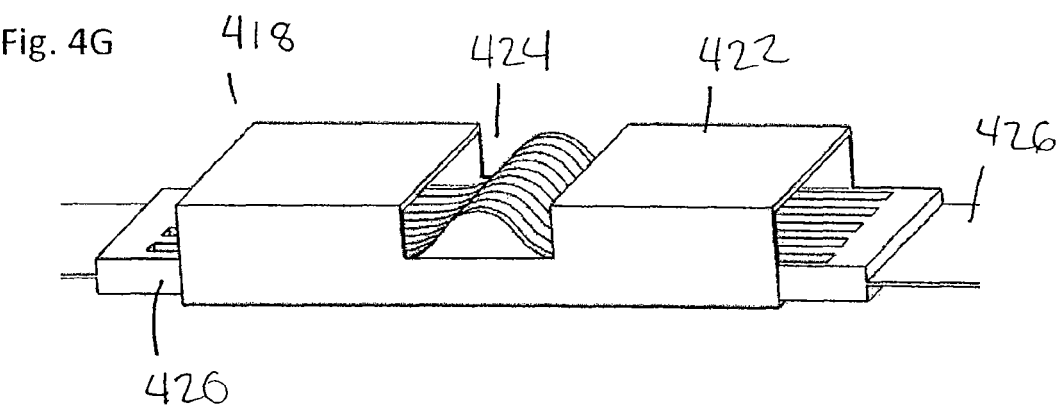

Additionally, the support member may include a holding structure, but need not. The holding structure may serve to at least partially enclose the at least one shaped plate (404). In some variations, the holding structure may have tracks, grooves, or inlets with which one or more shaped plate (404) may slidably engage. FIG. 4G shows one variation of support member (418) comprising shaped plates (420) housed within holding structure (422) defining aperture (424). Also shown there are attachment members (426). In this variation, the shaped plates (420) may slide between first and second positions within holding structure (422). As shaped plates (420) slide within holding structure (422), at least a portion of the shaped plates (420) may slide move through aperture (424) and thereby provide support to a target tissue above, near, or adjacent to aperture (424). In these variations, support member (418) may provide a constant amount of support along the boundary of holding structure (422) while providing dynamic support to a target tissue above, near, or adjacent to aperture (424). This may provide particular utility in instances where it is desirable to provide dynamic support to only one area, and constant support to other areas.

Furthermore, the support member may include one or more structures or components that may act to return the support member from its second configuration to its first configuration when a force is no longer being applied to the one or more attachment members. In some variations, the support member comprises an expandable membrane, a spring, a strip, band, or chord of elastic material, or another structure that may become stretched when the support member is in its second configuration. In these variations, the expandable membrane or other return structure may have a natural tendency to return to its un-stretched state, and may provide a restorative force to the support member. This restorative force, in turn, may help to return the support member to its first configuration. Alternatively, the support member may include a spring or other structure that is compressed or other accumulates a return force energy when the support member is moved to its second configuration. Similarly, the spring or other restorative force may have a natural tendency to return to its un-compressed state, and may also provide a restorative force to the support member.

The expandable membrane or other return structure may be made of any biocompatible material that is sufficiently elastic to allow the support member to change from its first configuration to its second configuration. In some variations, however, the expandable membrane or other return structure may act to limit the extent to which the support member may move between its configurations. In some variations, the expandable membrane or other return structure may be made from a material that is capable of returning to its original size and shape after it has been stretched. In some variations, the expandable membrane or other return structure comprises a mesh.

Where the support member contains shaped plates, as described above, the expandable membrane or other return structure may be attached to the device in any number of suitable configurations. In some variations, the expandable membrane may connect two or more shaped plates. In other variations, the expandable membrane may connect two attachment members, or may attach a shaped plate to an attachment member. In variations in which the support device comprises a holding structure, the expandable membrane may connect a shaped plate to the holding structure, or may attach an attachment member to the holding structure.

Any of the support members described here may be made of any suitable biocompatible material. Examples of suitable biocompatible materials include, but are not limited to, silicone, polypropylene, polyethylene, polyester, polycarbonate, polyetheretherketone, polyurethane, polyvinyl chloride, polyethylene terephthalate, and stainless steel. In some variations, the materials include autologous tissue, homologous tissue, cadaveric tissue, xenograft tissue, collagen matrix materials, synthetic materials, and combinations thereof. In variations that include two or more shaped plates, the shaped plates may be made from different materials. In other variations, the shaped plates may be made from the same material.

In some variations, the support member may include a stimulus responsive material. The stimulus responsive material may be any material capable of changing its shape or orientation upon the application of a stimulus to that material. In variations that include sliding members, application of at least one stimulus to the support member may cause the sliding members to change shape or slide between a first position and a second position, or vice versa. The at least one stimulus may be one or more of a combination of any number of suitable stimuli, so long as they do not irreparably harm human tissue. Examples of suitable stimuli include, but are not limited to, changes in temperature, changes in pH, optical stimuli (including light), RF energy, microwave energy, electrical energy, magnetic energy, mechanical energy, and combinations thereof.

FIGS. 5A-5D show another variation of support member (500) comprising sliding members (502). Shown in FIG. 5A is a perspective view of support member (500) in a first configuration, comprising platform elements (504) which are slidably engagable with sliding members (502) which include tracks (506). Also shown there are attachment members (508). While shown in FIGS. 5A-5D as having strips of material (510), attachment members (508) may have any configuration of elements as described above. FIG. 5B shows a perspective view of support member (500) in its second configuration.

Generally, tracks (506) may slide from a first position to a second position when a force is applied to one or more of the attachment members (508). FIG. 5C shows a side view of support member (500) with tracks (506) in a first position. When a force is applied to one or more of the attachment members (508), the tracks (506) may slide from the first position to a second position, as shown in a side view in FIG. 5D. This movement of the tracks (506) between a first and a second position may cause platform elements (504) to slide within tracks (506). Depending on the configuration of tracks (506), this sliding may change the relative positioning of platform elements (504), which may in turn change support member (500) from a first configuration to a second configuration. For example, in the variation shown in FIGS. 5A-5D, when the tracks (506) move between their first and second positions, the platform elements (504) move away from each other, thereby increasing the space occupied by support member (500). This may, in turn, allow support member (500) to support or compress a target tissue.

While shown in FIGS. 5A-5D as having two tracks (506), support member (500) may have any suitable number of tracks. Indeed, support member (500) may have zero, one, or two or more tracks. Additionally, while shown in FIGS. 5A-5D as being approximately v-shaped, tracks (506) may have any suitable size, shape, or configuration. Indeed, tracks (506) may have a shape that is substantially half-circular, elliptical, or z-shaped. In variations where support member (500) has two or more tracks (506), tracks may have the same size, shape, or configuration, or may have different sizes, shapes, or configurations. The shape of tracks (506) may determine the positioning of platform elements (504) when support member (500) is in its first and second configurations. Thus tracks (506) may be configured to move platform elements (504) to certain positions, or may be configured to move platform elements (504) at a certain rate when support member (500) changes between its first and second configurations.

Similarly, while shown in FIGS. 5A-5D as having two platform elements (504), support member (500) may include any number of platform elements (504). Indeed, support member (500) may have zero, one, or two or more platform elements (504). Additionally, platform elements (504) may have any size, shape, or configuration. In some variations, platform elements (504) may be curved or parabolic in shape. Furthermore, platform elements (504) may have ridges, raised portions, recessed portions, or a combination thereof. In variations that include two or more platform elements (504), the platform elements (504) may have the same size, shape, or configuration, or may different sizes, shapes, and/or configurations.

Additionally, support member (500) may have one or more elements configured to help return support member (500) from its second configuration to its first configuration when a force is no longer being applied to the attachment members (508). Indeed, in some variations support member (500) may have an expandable membrane, a spring, a strip, band, or chord of elastic material, or a combination thereof, as described above. In these variations, the expandable membrane or other return structure may attach any combination of elements in support member (500). In some variations, the expandable membrane or other return structure connects two or more attachment members, two or more tracks, or two or more platform elements. In other variations, the expandable membrane or other return structure connects one or more attachment members to one or more tracks or platform elements, or connects one or more platform elements to one or more tracks. Additionally, support member (500) may include a cover, as described above, but need not.

Figure 6A:
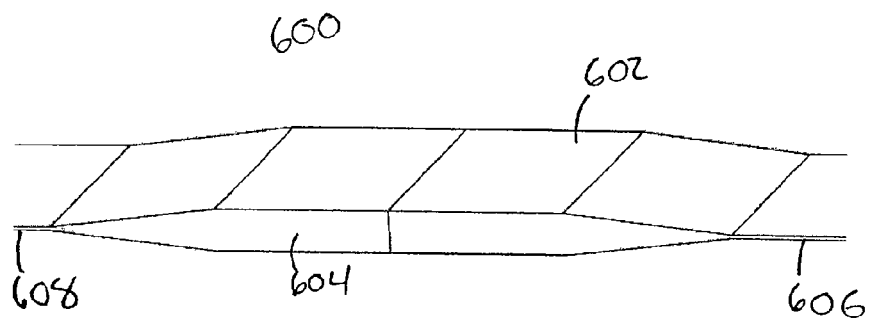
FIGS. 6A and 6B are perspective views of a variation of a support member having sliding members.
Figure 6B:
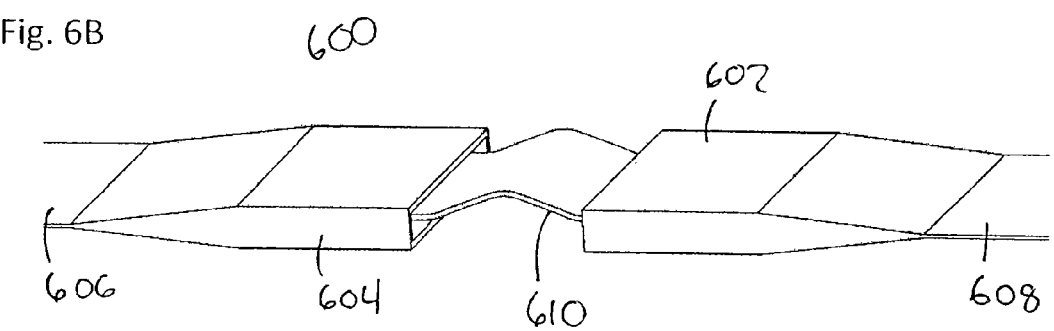

FIGS. 6A-6D illustrate yet another variation of support member (600) comprising sliding members (602). Shown in FIG. 6A is a perspective view of support member (600) in a first configuration, comprising attachment members (606) and sliding members (602). In the variations shown in FIGS. 6A-6D, sliding members (602) comprise housing components (604). While shown in FIGS. 6A-6D as having strips of material (608), attachment members (606) may have any combination of elements as described above. FIG. 6B shows a perspective view of support member (600) in its second configuration. Also shown there is internal component (610).

Figure 6C:
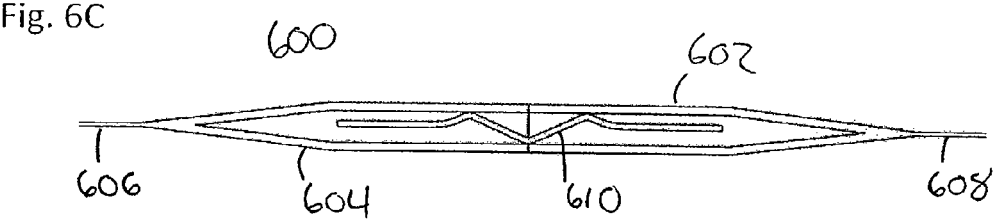
FIG. 6C is a cross-sectional side view and FIG. 6D is a side view of the support member shown in FIGS. 6A and 6B.
Figure 6D:
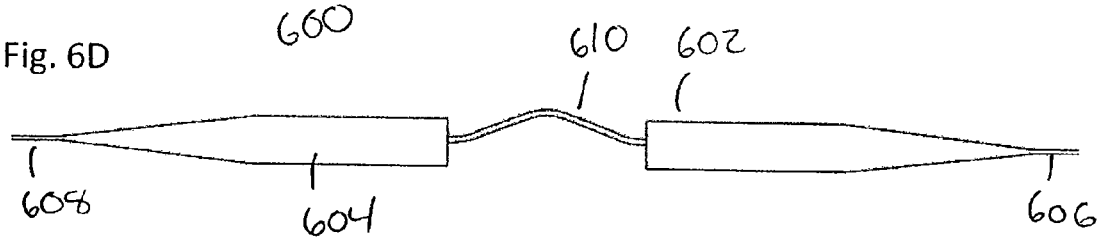

Generally, housing components (604) may slide from a first position to a second position when a force is applied to one or more of the attachment members. FIG. 6C shows a cross-sectional side view of support member (600) with housing components (604) in a first position. When housing components (604) are in a first position, internal component (610) may be at least partially enclosed in sliding member (602). When a force is applied to one or more of the attachment members (606), the housing components (604) may slide to a second position, as shown in a side view in FIG. 6D. This movement may expose at least a portion of internal component (610), which may change shape when the supporting member (600) is in its second configuration. This shape change may allow internal component (610) to apply a force to a target tissue, thereby allowing support member (600) to support the target tissue.

While shown in FIGS. 6A-6D as having one internal component (610), support member (600) may have any number of internal components (610). Indeed, support member (600) may have zero, one, or two or more internal components (610). Internal component (610) may have any size, shape, or configuration. In some variations, internal component (610) may be a filament or sheet made from a shape memory or other shape changing material that changes shape when support member (600) is in its second configuration. In other variations, the internal component (610) may be a balloon or other expandable device that expands when support member (600) is in its second configuration. Additionally, in some variations the internal component (610) is capable of returning to its original shape when the support member (600) returns from its second configuration to its first configuration. In some of these variations, the support member (600) naturally returns to its first configuration when a force is no longer being applied to the attachment members (606). In others of these variations, an additional stimulus or force may be required to return support member (600) to its first configuration when a force is no longer being applied to the attachment members (606).

Support member (600) may additionally comprise one or more features to help guide housing components (604) as they move between a first position and a second position, or vice versa. In some variations, support member (600) may comprise one or more tracks (not shown), but need not. These tracks may be slidably engagable with one or more housing components (604), and may act to guide the movement of one housing component (604) relative to another. Tracks may be located anywhere in or on support member (600). In other variations, internal component (610) may be sized or shaped such that it guides the movement of the housing components (604). For example, if the width of internal component (610) is large enough such that it abuts the inner boundaries of the housing components (604), the internal component (610) may prevent the housing components (604) from moving laterally relative to the internal component (610).

In other variations, housing components (604) may be connected by an expandable membrane or other return structure as described above. When the expandable membrane or other return structure connects housing components (604), the expandable membrane or other return structure may act to guide housing components (604) as they move between a second position and a first position. Additionally, in some variations the expandable membrane or other return structure may limit or otherwise constrain the movement of the housing components (604). In some variations, an expandable membrane or other return structure may connect housing components (604) such that the expandable membrane or other return structure completely surrounds internal component (610) and seals off the interior of housing components (604). In these variations, the expandable membrane or other return structure may act as a cover. In still other variations, support member (600) may comprise a cover, as described above, but need not.

It should be noted that the expandable membrane or other return structures may connect any combination of elements of support member (600). Indeed, in some of these variations, the expandable membrane or other return structure may connect two or more attachment members (606), two or more housing components (604), two or more internal components (610), or two or more tracks (in variations that include tracks). In other variations, the expandable membrane or other return structure may connect one or more attachment members to one or more housing components (604), internal components (610), or tracks. In still other variation, the expandable membrane or other return structure may connect one or more housing components (604) to one or more internal components (610) or tracks. In yet other variations, the expandable membrane may connect one or more internal components (610) to one or more tracks.

In some variations of the support devices described here, at least a portion of the support member is configured to rotate when a force is applied to one or more of the attachment members. In some variations, the application of force to one or more of the attachment members causes the entire support member to rotate. In other variations, the application of force to one or more attachment member causes one or more portions of the support member to rotate. Generally, the rotation of a support member or a component of a support member may change the support member from a first configuration to a second configuration. In some of these variations, the support member may apply a force to a target tissue when the support member is in its second configuration.

Figure 7A:
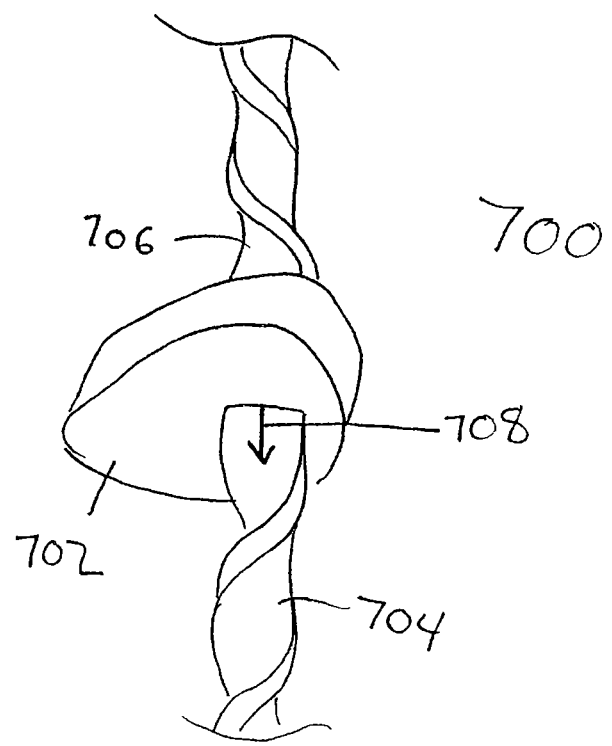
FIGS. 7A and 7B are perspective views of a variation of a support member that may be configured to rotate.
Figure 7B:
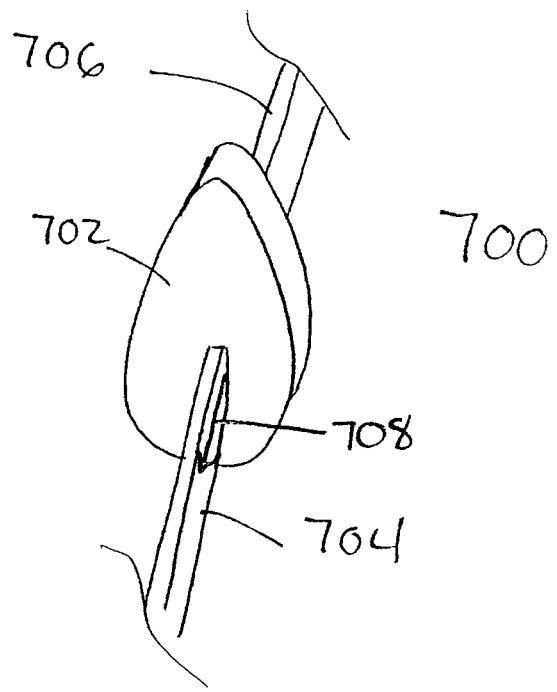

FIGS. 7A and 7B show one variation of support device (700) that comprises a support member (702) capable of rotating upon application of force to one or more attachment members (704). While shown in FIGS. 7A and 7B as having strips of material (706), attachment members (704) may have any configuration of elements as described above. FIG. 7A shows a perspective view of support device (700) in a first configuration. When support device (700) is in its first configuration, attachment members (704) may be twisted. When a force is applied to one or more of attachment members (704), the attachment members (704) may have a tendency to un-twist. As the attachment members (704) un-twist, the attachment members (704) may in turn rotate the support member (702) around an axis of rotation (708), thereby changing support device (700) to a second configuration, as shown in FIG. 7B. In some variations, the axis of rotation (708) may be substantially parallel to attachment members (704) near the point of attachment between attachment members (704) and support member (702). In some variations, support member (702) may apply a force to a target tissue when the support device (700) is in its second configuration.

In some variations, support device (700) may naturally return to its first configuration when a force is no longer being applied to the attachment members (704). In other variations, the support device (700) includes one or more components that may act to return the support member to its first configuration. In other variations, one or more forces or stimuli may be necessary to return support device (700) to its first configuration. In some of these variations, the one or more forces or stimuli may be provided by the external environment surrounding the support device. In some variations, attachment members (704) may be made from a stimulus responsive material that has a tendency to twist or un-twist when a one or more stimuli are applied to the attachment members (704). In these variations, one or more stimuli as described above may be applied to attachment members (704) to change support device (700) between its first and second configurations.

While shown in FIGS. 7A and 7B as having an oblong cross-section, support member (702) may have any size, shape, or configuration. Examples of suitable cross-sectional shapes include, but are not limited to, circles, ellipses, triangles, rectangles, polygons, shapes with irregular geometry and the like. Additionally, support member (700) may comprise a cover, as described above, but need not.

Figure 8A:
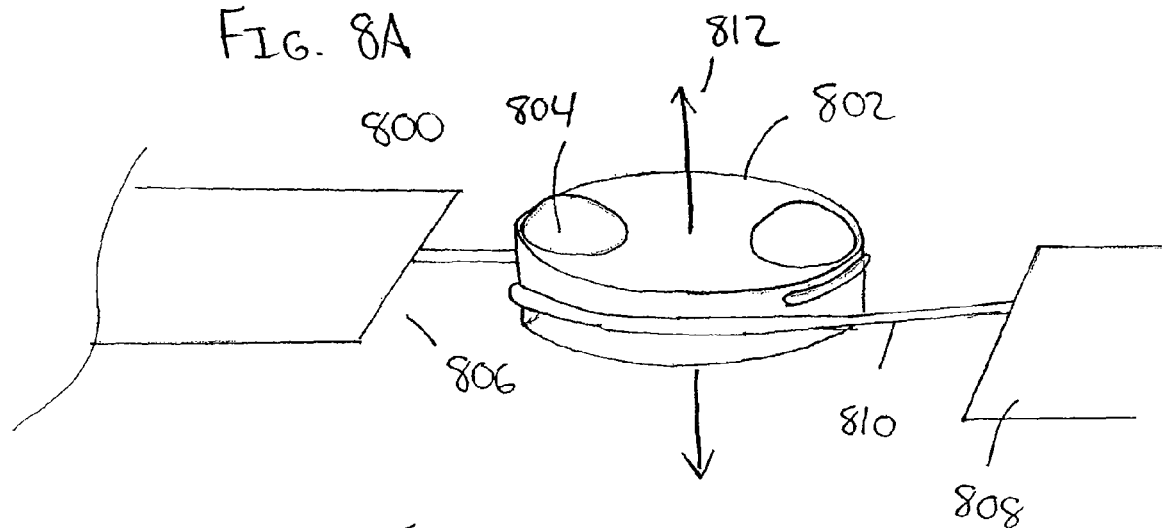
FIG. 8A is a perspective view of a variation of a support member that may be configured to rotate.
Figure 8B:
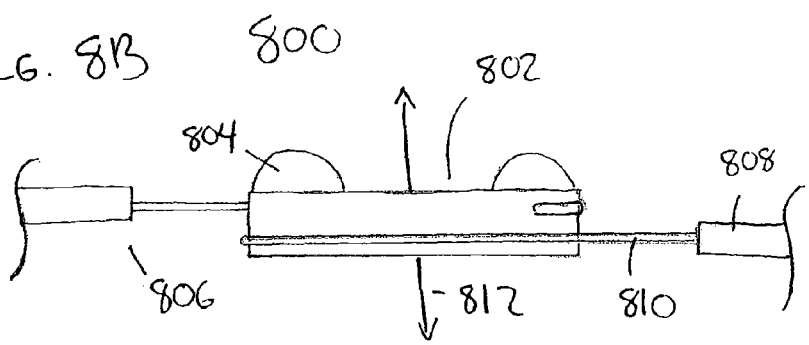
FIGS. 8B and 8C are side views of the support member shown in FIG. 8A.
Figure 8C:
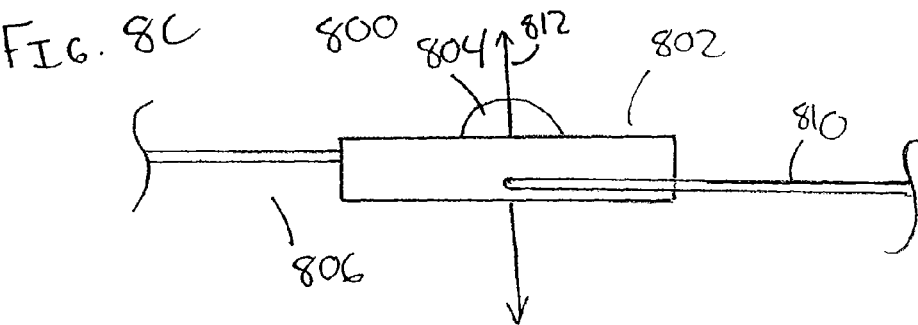

FIGS. 8A-8C show another variation of support device (800) comprising a support member (802) that may be configured to rotate. FIG. 8A shows a perspective view of support device (800) in a first configuration, comprising support member (802) with elevated sections (804) and attachment members (806). While shown in FIGS. 8A-8C as having strips of material (808) and connection members (810), attachment members (806) may have any suitable configuration of elements as described above.

Generally, when support device (800) is in its first configuration, one or more portions of one or more the attachment members (806) may be at least partially wound around at least a portion of support member (802). For example, in FIG. 8B the connection members (810) of attachment members (806) are at least partially wound around support member (802). When a force is applied to one or more of the attachment members (806), the attachment members (806) may in turn apply a tensile or rotational force to support member (802). This may cause support member (802) to rotate around an axis of rotation (812). This rotation may cause the relative positioning of elevated sections (804) to change, thereby changing support device (800) to a second configuration, as shown in a side view in FIG. 8C. In some variations, the elevated sections (804) may be positioned underneath a target tissue when the support device (800) is in its second configuration, and may apply a force to a target tissue when the support device (800) is in its second configuration. In some of these variations, direction of the force applied by the support device (800) may be substantially parallel to the axis of rotation (812) of support member (802).

While shown in FIGS. 8A-8C as having elevated sections (804), support member (802) need not. In variations that do include elevated sections (804), support member (802) may have any number of elevated sections (804). Additionally, elevated sections (804) may have any size, shape, or configuration. In variations that include two or more elevated sections (804), the elevated sections (804) may have the same size, shape, and configurations, or may have different sizes, shapes, or configurations. In some variations, the elevated sections (804) may be configured to linearly increase the amount of support provided by support member (802) to a target tissue as support device (800) changes between its first and second configurations. Additionally, in some variations support device (800) may comprise a cover, as described above, but need not. In some variations, support device (800) may naturally return to its first configuration when a force is no longer being applied to the attachment members (806). In other variations, the support device (800) includes one or more components that may act to return the support member to its first configuration. In other variations, one or more forces or stimuli may be necessary to return support device (800) to its first configuration. In some of these variations, the one or more forces or stimuli may be provided by the external environment surrounding the support device.

Figure 9A:
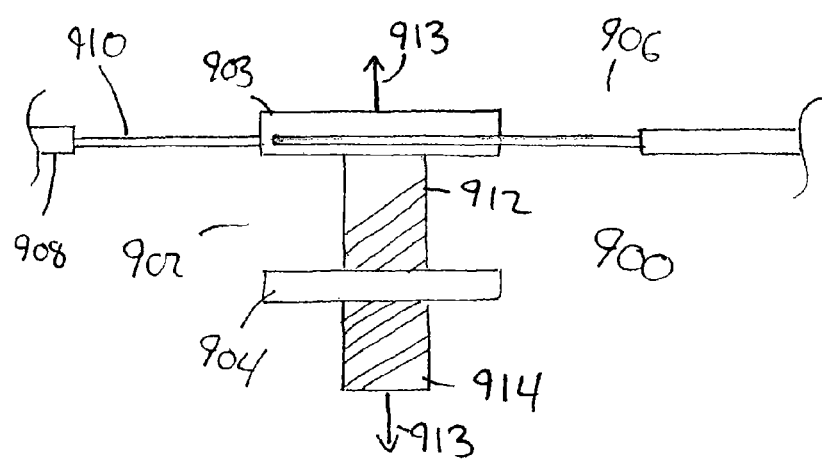
FIGS. 9A and 9B are side views of a variation of a support member that may be configured to rotate.
Figure 9B:
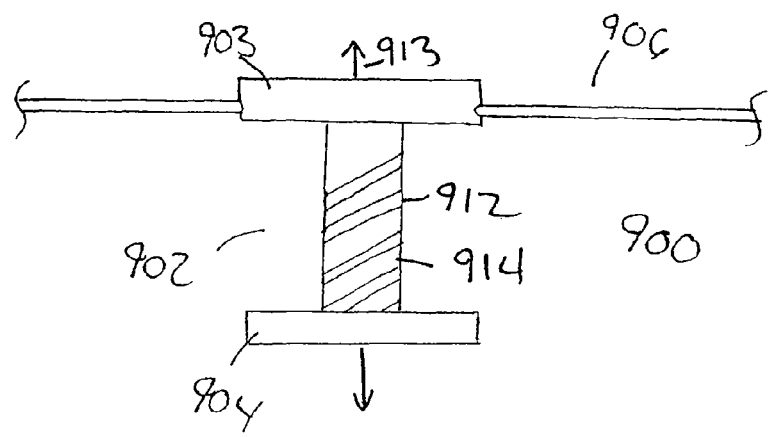

In some variations, the height of the support member may change as the support member or a component of support member rotates. FIGS. 9A and 9B show one such variations of support device (900). FIG. 9A shows a side view of support device (900) in a first configuration comprising support member (902) with head (903) and base portion (904). Also shown there are attachment members (906) attached to support member (902). While shown in FIGS. 9A-9C as having strips of material (908) and connection members (910), attachment members (906) may have any suitable configuration of elements as described above.

When support device (900) is in a first configuration, one or more attachment members (906) may be at least partially wound at least a portion of support member (902), as shown in FIG. 9A. Additionally, support member (902) may have threading (912), which may be rotatably engagable with threading (not shown) in base portion (904). When a force is applied to one or more attachment members (906), attachment members (906) may apply a force to support member (902). This force cause support member (902) to rotate around axis of rotation (913). As support member (902) rotates, the height of head (903) relative to base portion (904) may either increase or decrease, changing support device (900) from a first configuration to a second configuration, as shown in FIG. 9B. In some variations, the support member (902) applies a supporting force to a target tissue when the support device (900) is in its second configuration. In some variations, the direction of this supporting force may be substantially parallel to the axis of rotation (913).

While shown in FIGS. 9A and 9B as having a head (903), supporting member (902) need not. In variations that do include a head (903), head (903) may have any size, shape, or configuration. For example, in some variations, head (903) may have a rounded top. In other variations, head (903) may include one or more elevated sections or recessed sections, as described above. Additionally, in some variations support device (900) comprises a cover, as described above, but need not.

While shown in FIGS. 9A and 9B as being attached to head (903), attachment members (906) may be attached to support member (902) in any suitable manner. In some variations, attachment members (906) may be attached to the body (914) of support member (902). In some of these variations, attachment members (906) may attach to support member (902) through holes (not shown) in base portion (904). In other variations, attachment members (906) may attach to support member (902) through grooves or channels (not shown) located on one or more surfaces of base portion (904). Additionally, in some variations, support device (900) may naturally return to its first configuration when a force is no longer being applied to the attachment members (906). In other variations, the support device (900) includes one or more components that may act to return the support member to its first configuration. In other variations, one or more forces or stimuli may be necessary to return support device (900) to its first configuration. In some of these variations, the one or more forces or stimuli may be provided by the external environment surrounding the support device.

Figure 10A:
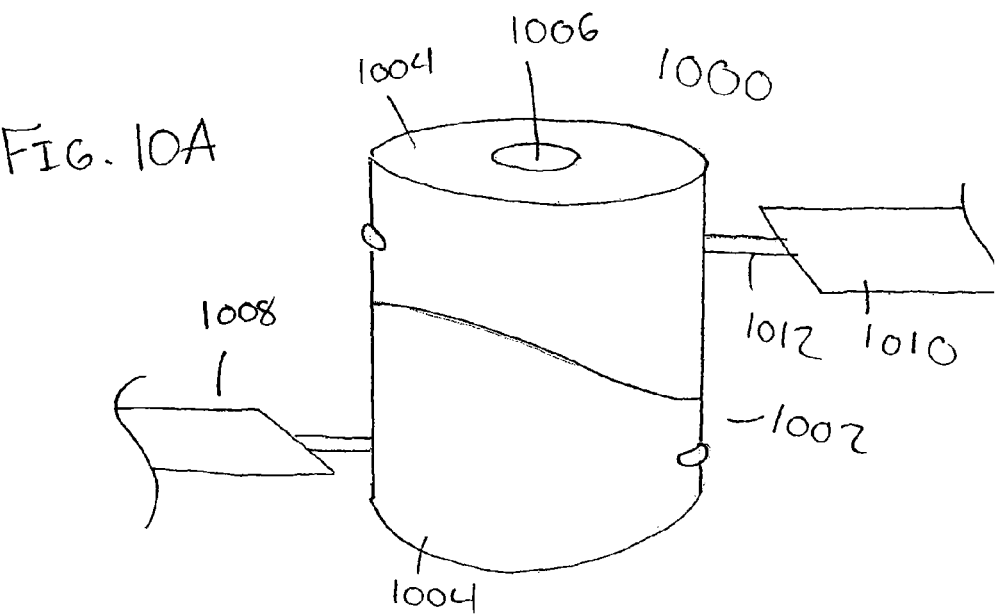
FIG. 10A is a perspective view of one variation of a support device having at least one rotating component.
Figure 10B:
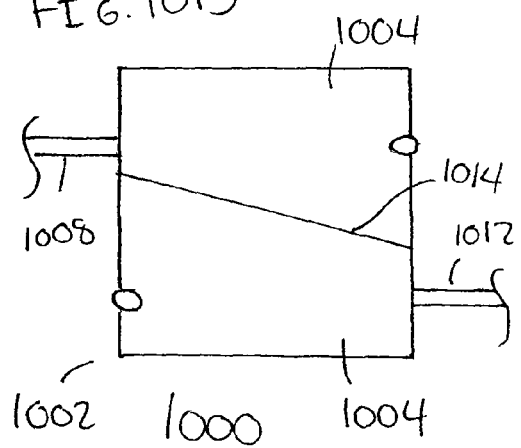
FIGS. 10B and 10C are side views of the support device shown in FIG. 10A.
Figure 10C:
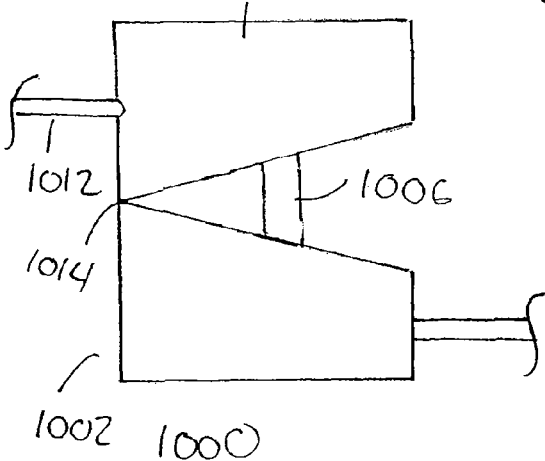

FIGS. 10A-10C show another variation of support device (1000) including a support member (1002) that may change height as one or more of its components rotate. FIG. 10A shows a perspective view of support device (1000) in a first configuration, comprising support member (1002) having rotating components (1004) and pin (1006). Also shown there are attachment members (1008). While shown in FIGS. 10A and 10B as having strips of material (1010) and connection members (1012), attachment members (1008) may have any suitable configuration of elements as described above.

Generally, each attachment member (1008) is attached to at least a portion of at least one rotating component (1004). In some variations, one or more attachment members (1008) are at least partially wound around at least a portion of at least one rotating component (1004). Generally, one or more rotating components (1004) may be both rotatably engagable, slidably engagable or both rotatably and slidably engagable with pin (1006). Additionally, each rotating component (1004) may touch another rotating component (1004) at one or more contact points (1014). When support device (1000) is in a first configuration, the contact point (1014) between the two rotating components (1004) may include an entire surface of the rotating components (1004), as shown in a side view in FIG. 10B.

When a force is applied to one or more of the attachment members (1008), one or more of the rotating components (1004) may rotate around pin (1006). This rotation may be constrained by both the pin (1006) and the contact point (1014). More specifically, pin (1006) may prevent the rotating components (1014) from moving laterally relative to each other, while contact point (1014) determines the relative height of rotating components (1014). Thus, as one or more of the rotating components (1004) rotates around pin (1006), the contact point (1014) may change and thereby change the overall height of support member (1002). This rotation may change support device (1000) from a first configuration to a second configuration, as shown in FIG. 10C. In some variations, the support member (1002) may provide a force to a target tissue when the support device (1000) is in its second configuration. In some of these variations, this force may be substantially parallel to pin (1006).

While shown in FIGS. 10A and 10B as being complimentary halves of a cylinder, rotating components (1004) may have any suitable size, shape, or configuration, which need not be the same for each rotating component (1004). Additionally, support member (1002) may have any number of rotating components (1004) or other components. Furthermore, in some variations, some of the components may be complimentary, but need not be. In some variations, rotating components (1004) may be complimentary halves of a sphere, a box, or any other shape which occupies a volume. Additionally, in some variations support device (1000) may comprise a cover, as described above. In some variations, support device (1000) may naturally return to its first configuration when a force is no longer being applied to the attachment members (1008). In other variations, the support device (1000) includes one or more components that may act to return the support member to its first configuration. In other variations, one or more forces or stimuli may be necessary to return support device (1000) to its first configuration. In some of these variations, the one or more forces or stimuli may be provided by the external environment surrounding the support device.

Figure 11A:
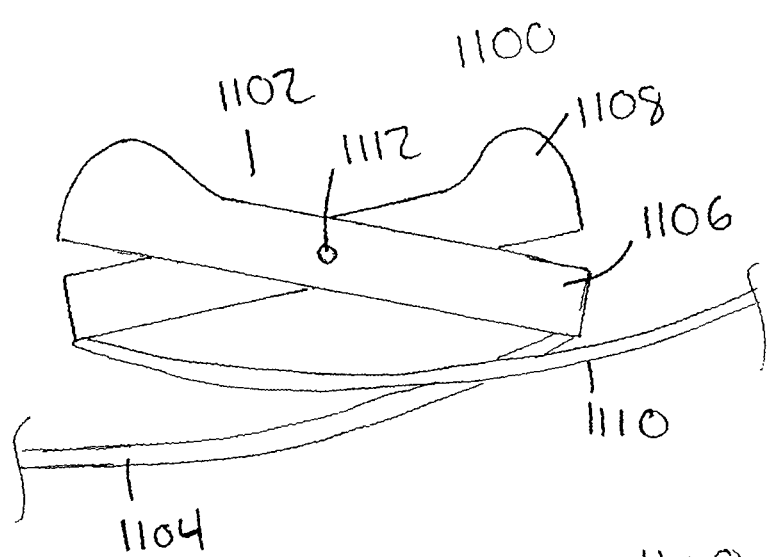
FIGS. 11A and 11B are side views of one variation of a support device having rotating plates.
Figure 11B:
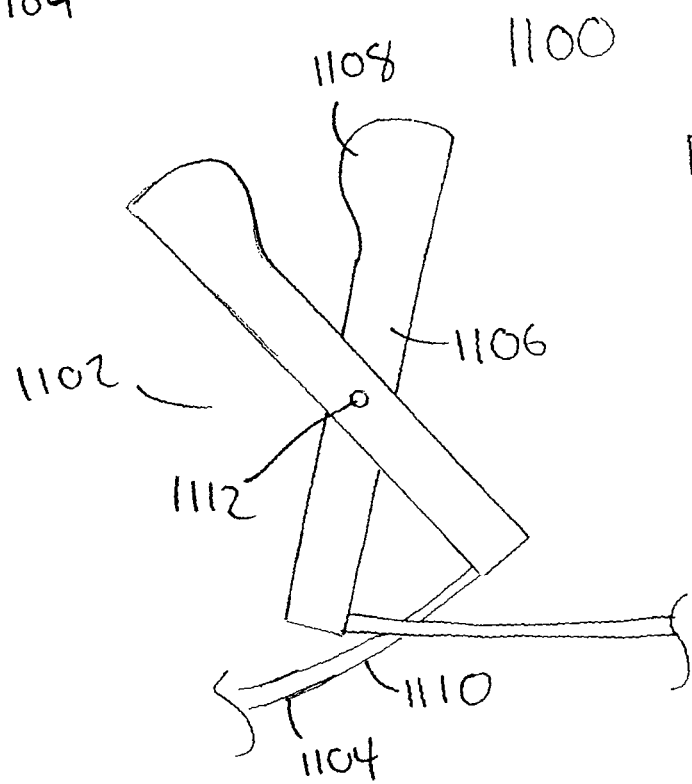

FIGS. 11A and 11B show another variation of support device (1100) having a support member (1102) that has components that may be configured to rotate upon application of a force to one or more attachment members (1104). FIG. 11A shows a side view of support device (1100) in a first configuration. Shown there are attachment members (1104) and support member (1102) comprising rotating plates (1106) with elevated sections (1108). While shown in FIGS. 11A and 11B as having strips of material (1110), attachment members (1104) may have any suitable configuration of elements as described above. Attachment members (1104) may be attached to one or more rotating plates (1106) at any suitable point along their lengths. Furthermore, rotating plates (1106) may be able to rotate relative to each other at hinge point (1112).

Support device (1100) may be configured such that when a force is applied to one or more attachment members (1104), one or more rotating plates (1106) may rotate relative to hinge point (1112). This rotation may cause support device (1100) to change from its first configuration to a second configuration, as shown in FIG. 11B. In some variations, rotating plates (1106) may provide support to a tissue located above one or more of the rotating plates (1106). In other variations, a target tissue may be compressed between two or more rotating plates (1106).

While shown in FIGS. 11A and 11B as having two rotating plates (1106), support device (1100) may have any number of rotating plates (1106). Indeed, support device (1100) may have zero, one, two, or three or more rotating plates (1106). Additionally, rotating plates (1106) may have any suitable size, shape or configuration. For example, rotating plates (1106) may have zero, one, or two or more elevated sections (1108), may have zero, one, or two or more recessed sections, or may have a combination thereof. In some variations, the support device (1100) may comprise a cover, as described above, but need not. In some variations, support device (1100) may naturally return to its first configuration when a force is no longer being applied to the attachment members (1104). In other variations, the support device (1100) includes one or more components that may act to return the support member to its first configuration. In other variations, one or more forces or stimuli may be necessary to return support device (1100) to its first configuration. In some of these variations, the one or more forces or stimuli may be provided by the external environment surrounding the support device.

Figure 12A:
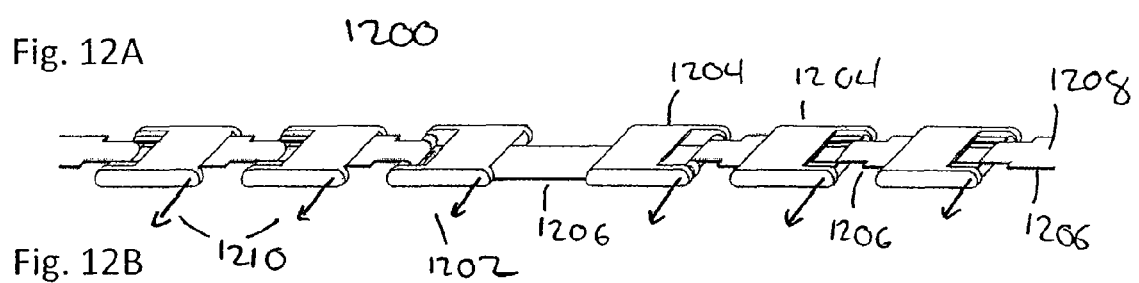
FIGS. 12A and 12B are perspective views of one variation of a support device having rotating arms.

FIGS. 12A-12D show another variation of support device (1200) comprising a support member (1202) that includes one or more rotating arms (1204). FIG. 12A shows a perspective view of support device (1200) in a first configuration. Also shown there are attachment members (1206) and rotating arms (1204). While shown in FIGS. 12A-12D as having strips of material (1208), attachment members (1206) may have any suitable configuration of elements as described above. Generally, each rotating arm (1204) is configured to rotate around an axis of rotation (1210). When a force is applied to one or more attachment members, rotating arms (1204) may rotate around their respective axes of rotations (1210), thereby changing support device (1200) from a first configuration to a second configuration, as shown in a perspective view in FIG. 12B. One or more of the rotating arms (1204) may provide support to one or more target tissues when the support device (1200) is in its second configuration.

Rotating arms (1204) may be configured to rotate in any number of ways. FIG. 12C show one variation of rotating arm (1212) comprising bar (1214) passing through axis of rotation (1216). In some of these variations a first attachment member (1218) may be attached to and partially coiled around bar (1214). In some of these variations, a second attachment member (1220) may be attached around bar (1214) such bar (1214) may rotate within second attachment member (1220). In these variations, when a force is applied to one of the attachment members, first attachment member (1218) may have a tendency to uncoil, and this uncoiling may cause rotating arm (1212) to rotate relative to axis of rotation (1216). FIG. 12D shows another variation of rotating arm (1222) comprising bar (1224) passing through axis of rotation (1226), and attachment member (1228) completely coiled around bar (1224). In some of these variations, attachment member (1228) may also pass through slit (1230) within bar (1224), which may help to affix attachment member (1228) to bar (1224). Again, when a force is applied to attachment member (1228), attachment member (1228) may have a tendency to uncoil and rotate rotating arm (1222).

Figure 12B:
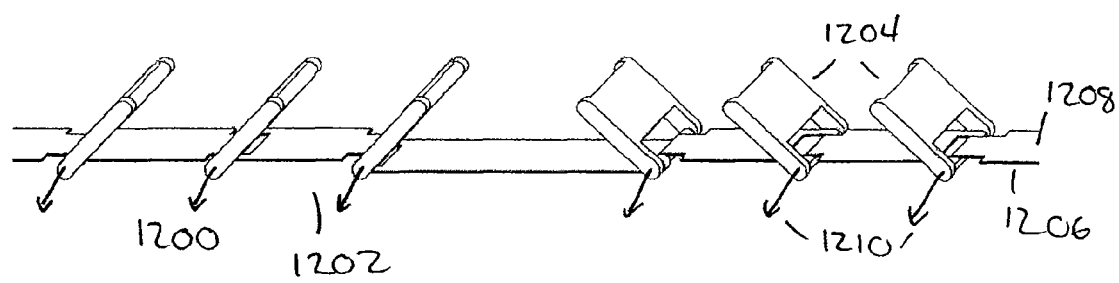
Figure 12C:
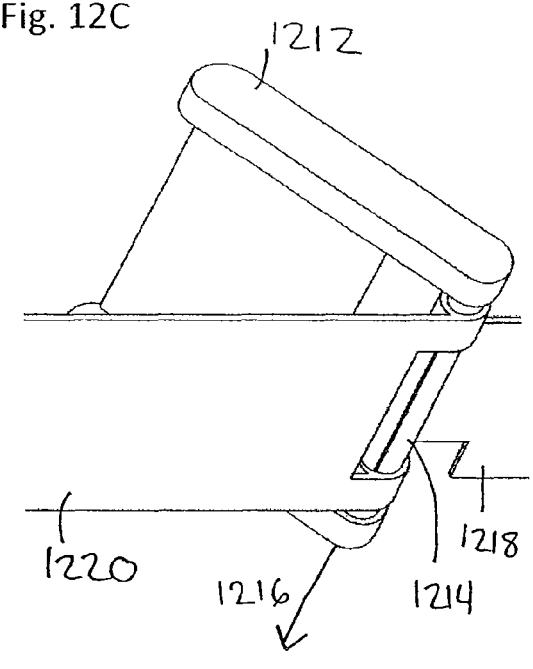
FIGS. 12C and 12D are perspective views of two variations of rotating arms.
Figure 12D:
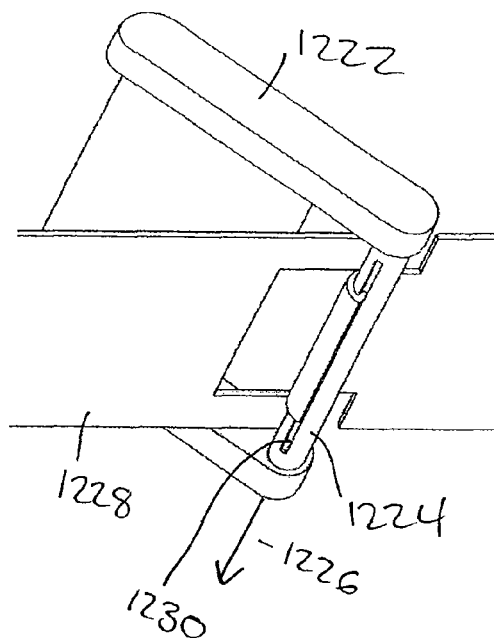

While shown in FIGS. 12A and 12B as having a plurality of rotating arms (1204), support device (1200) may have any number of rotating arms (1204). Support device (1200) may have zero, one, two, three, four, five, or six or more rotating arms (1204). While shown in FIGS. 12A and 12B as having rotating arms (1204) that are configured to rotate both clockwise and counterclockwise around their respective axes of rotation (1210), support device (1200) need not. Indeed, in some variations, support device (1200) may comprise only rotating arms (1204) configured to rotate clockwise around their respective axes of rotation (1210), or only rotating arms (1204) configured to rotate counterclockwise around their respective axes of rotation (1210). In some variations, support device (1200) may comprise a cover, as described above, but need not. In some variations, support device (1200) may naturally return to its first configuration when a force is no longer being applied to the attachment members (1204). In other variations, the support device (1200) includes one or more components that may act to return the support member to its first configuration. In other variations, one or more forces or stimuli may be necessary to return support device (1200) to its first configuration. In some of these variations, the one or more forces or stimuli may be provided by the external environment surrounding the support device.

Figure 13A:
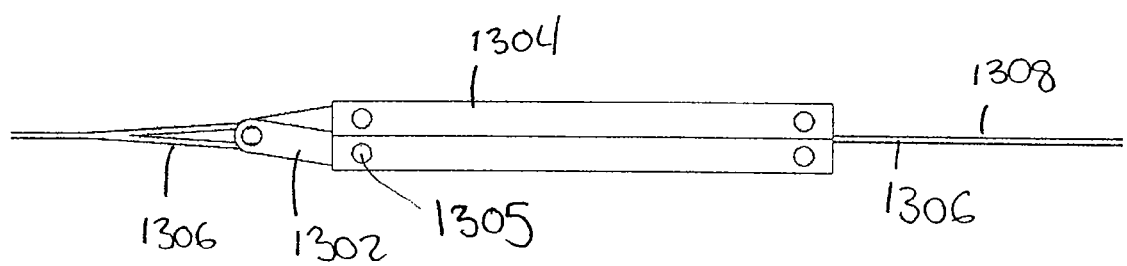
FIGS. 13A and 13B are side views of one variation of a support device having rotating arms and platform elements.
Figure 13B:
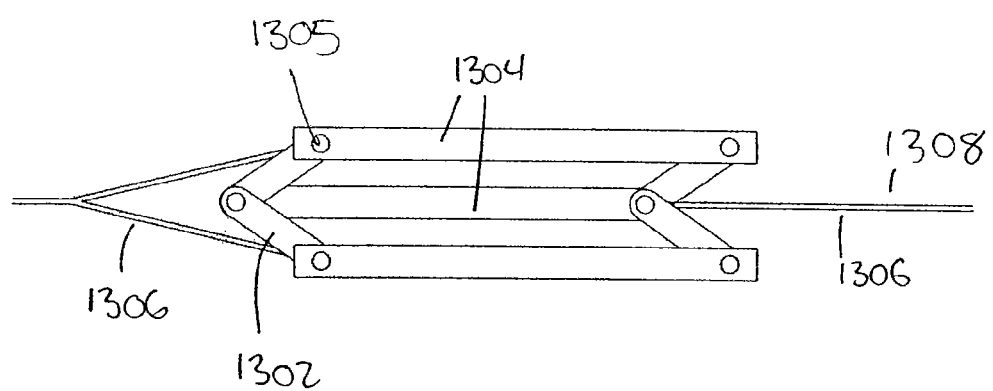

FIGS. 13A and 13B show another variation of support device (1300). FIG. 13A shows a side view of support device (1300) in a first configuration. Shown there are rotating arms (1302), platform elements (1304), and attachment members (1306). While shown in FIGS. 13A and 13B as having strips of material (1308), attachment members (1306) may have any suitable configuration of elements as described above. Rotating arms (1302) may be rotatably connected to one or more platform elements (1304) such that rotating arms (1302) may rotate relative to the one or more platform elements (1304). In some variations, rotating arms (1302) comprise a pin (1305) or bar that are rotatably engagable with one or more platform elements (1304). In other variations, pin (1305) or bar is rotatably engagable with both rotating arms (1302) and platform elements (1304). Additionally, each attachment member (1306) may be attached to one or more platform elements (1304) one or more rotating arms (1302), or one or more pins (1305) or bars. When a force is applied to one or more attachment members (1306), one or more rotating arms (1302) may rotate relative to one or more platform elements (1304). In some variations, this rotation may cause one or more platform elements (1304) to change their positioning, and thereby change support device (1300) from a first to a second configuration, as shown in FIG. 13B.

Support device (1300) may have any number or combination of rotating arm (1302) and any number of platform elements (1304). Rotating arms (1302) may have any size, shape, or configuration. In variations that have multiple rotating arms (1302), the rotating arms (1302) may have the same size, shape, and configuration, or may have different sizes, shapes, and configurations. Similarly, platform elements (1304) may have any size, shape, or configuration as described above. In variations that have multiple platform elements (1304), the platform elements (1304) may have the same size, shape, and configuration, or may have different sizes, shapes, or configurations.

Additionally, support device (1300) may have one or more elements configured to help return support device (1300) from its second configuration to its first configuration when a force is no longer being applied to the attachment members (1306). Indeed, in some variations support device (1300) may have an expandable membrane, a spring, a strip, band, or chord of elastic material, or a combination thereof, as described above. In these variations, the expandable membrane or other return structure may attach any combination of elements in support device (1300). In some variations, the expandable membrane or other return structure connects two or more attachment members, two or more rotating arms, or two or more platform elements. In other variations, the expandable membrane or other return structure connects one or more attachment members to one or more rotating arms or platform elements, or connects one or more platform elements to one or more rotating arms. Additionally, support device (1300) may include a cover, as described above, but need not. In some variations, support device (1300) may naturally return to its first configuration when a force is no longer being applied to the attachment members (1306). In other variations, the support device (1300) includes one or more components that may act to return the support member to its first configuration. In other variations, one or more forces or stimuli may be necessary to return support device (1300) to its first configuration. In some of these variations, the one or more forces or stimuli may be provided by the external environment surrounding the support device.

In some variations of the dynamic support devices described here, one or more supporting members comprise one or more deformable components. Generally, the deformable component changes shape when one or more forces are applied thereto. In some variations, the one or more forces may be tensile forces. In other variations, the one or more forces may be compressive forces. In still other variations, the one or more forces may be a combination of tensile and compressive forces. In some variations, the application of a force to one or more attachment members may result in the application of one or more forces to the deformable component. The shape change resulting from the application of one or more forces to the deformable component may change the one or more support members from a first configuration to a second configuration. In some variations, the one or more support members may apply a force to a target tissue when it is in its second configuration.

Figure 14A:
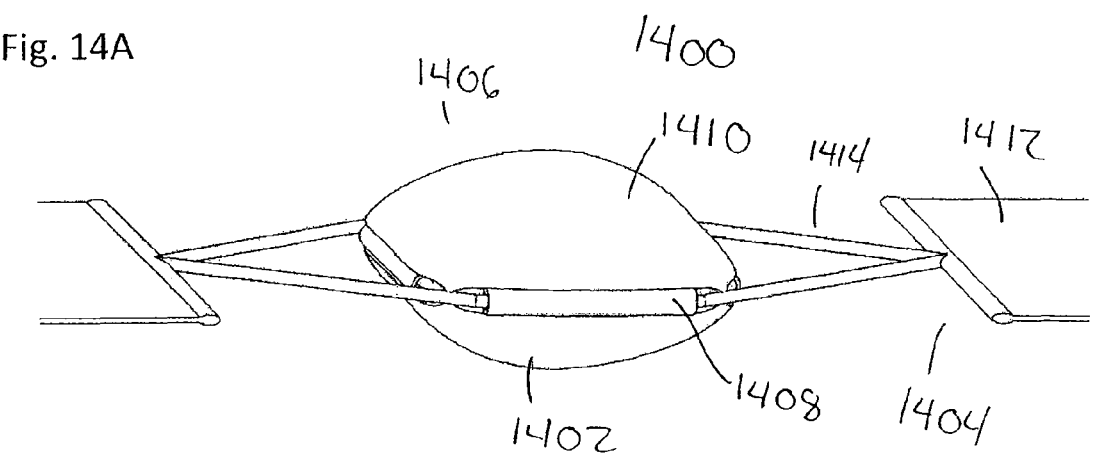
FIG. 14A is a perspective view of one variation of a support device having at least one deformable component.
Figure 14B:
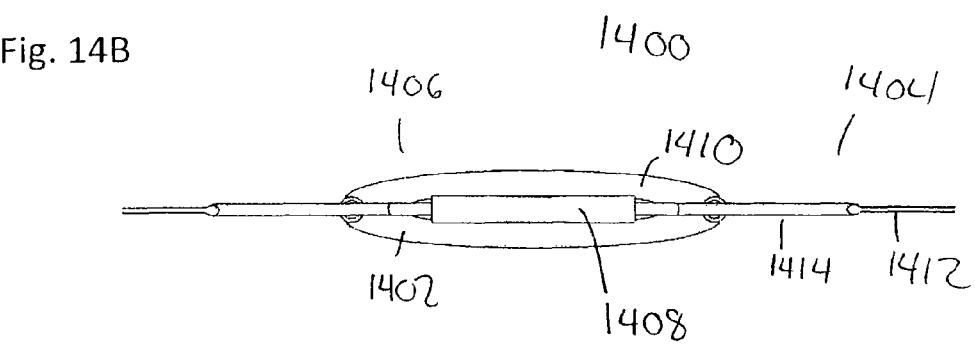
FIGS. 14B and 14C are side views of the support device shown in FIG. 14A.
Figure 14C:
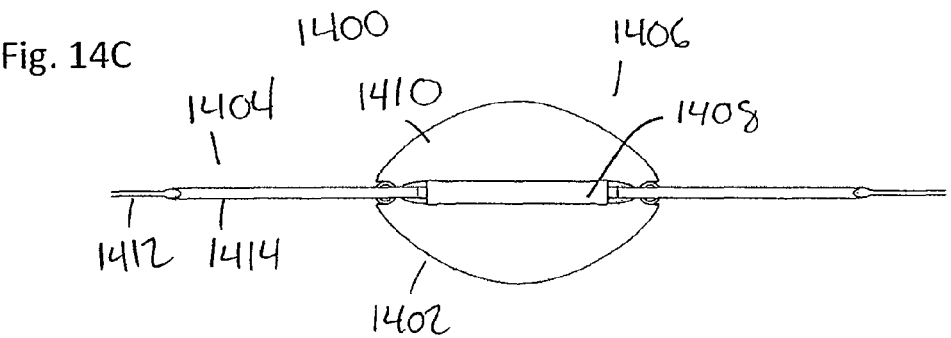

In variations in which the support member comprises one or more deformable components, the support member may include any number of deformable components. Indeed, support member may have zero, one, or two or more deformable components. Similarly, the deformable component may have any size, shape, or configuration. Indeed, FIGS. 14A-14C show one suitable variation of support device (1400) having deformable component (1402). FIG. 14A shows a perspective view of support device (1400) in a first configuration, comprising attachment members (1404), support member (1406) comprising deformable component (1402), and framing elements (1408). In the variations shown in FIGS. 14A-14C, deformable component (1402) is a shaped structure (1410) of a deformable material. While shown in FIGS. 14A-14C as having strips of material (1412) and connection members (1414), suitable attachment member (1404) may have any suitable configuration of elements as described above.

In some variations, the attachment members (1404) may be configured to wrap around shaped structure (1410), as shown in FIG. 14A and in a side view in FIG. 14B. When a force is applied to one or more of the attachment members (1404), the attachment members (1404) may compress a portion of shaped structure (1410). This compression may at least partially deform shaped structure (1410), thereby changing its shape, as shown in FIG. 14C. In some variations, this deformation may increase the overall height of shaped structure (1410). By changing the height of shaped structure (1410), the support member (1406) may provide increased or decreased support to a target tissue. In some variations, shaped structure (1410) is reversibly deformable, and naturally returns to its original shape when a force is no longer being applied to the attachment members (1404). In other variations, an additional force or stimulus may be used to return the shaped structure (1410) to its original shape when a force is no longer being applied to the attachment members (1404). In some of these variations, the external environment surrounding the support device (1400) may provide the additional force or stimulus. In some variations, support device (1400) has one or more components that may act to return shaped structure (1410) to its original shape when a force is no longer being applied to the attachment members (1404).

Shaped structure (1410) can be made of any suitable deformable material. Examples of suitable materials include, but are not limited to rubbers: buna-N, Butly, ECH (epichlorohydrin), EPDM (ethylene-propylene-diene monome), Gum, Hypalon, Latex, Neoprene, Polyurethane, Santoprene, SBR (styrene butadiene), Silicone, Vinyl, Viton, (or any foamed version of the previously listed); Hydrogel materials including: polymeric hydrogels or hydrogels of methacrylic acid composition; collagen scaffolds, collagen matrix, biocompatible scaffold or matrix, Polyethylene glycol (PEG) infused materials, semi-permeable membrane material, or bioabsorbable materials. In some variations, shaped structure (1410) may be made entirely from a single material or combination materials. In other variations, shaped structure (1410) may be hollow. In some of these variations, shaped structure (1410) may house a fluid therein. In some variations, the fluid may comprise a gas, such as, but not limited to, air, oxygen, nitrogen, an inert gas, or a combination thereof. In other variations, the fluid may comprise a liquid such as, but not limited to water, saline, a biocompatible liquid, or solution containing antibiotics, or a combination thereof. In still other variations, the fluid may comprise a combination of one or more liquids and one or more gasses.

While shown in FIGS. 14A-14C as having framing elements (1408), support device (1400) need not. Framing elements (1408) may be attached to shaped structure (1410), but need not be. In variations that do include framing elements (1408), framing elements (1408) may be used to help hold attachment members (1404) in a proper positioning relative to shaped structure (1410). Additionally, framing elements (1408) may guide the deformation of shaped structure (1410). In some variations, changing size or shape of framing elements (1408) may change the amount or direction of deformation of the shaped structure (1410) when a force is applied to one or more of the attachment members. For example, increasing the surface area of framing elements (1408) that contact shaped structure (1410) may increase the amount that shaped structure (1410) deforms when subjected to one or more forces. Additionally, support device (1400) may comprise a cover, as described above, but need not.

FIGS. 15A-15C illustrate another suitable variations of support device (1500) comprising a support member (1502) that comprises one or more deformable components (1504). FIG. 15A shows a perspective of view of support device (1500) including attachment members (1506), plates (1508) and deformable component (1504) comprising bellows (1510). While shown in FIGS. 15A-15C as having strips of material (1512) and connection members (1514), attachment members (1506) may have any suitable configuration of elements as described above.

Generally, attachment members may be attached to one or more plates (1508) at connection points (1516), as shown in a top view in FIG. 15B. When a force is applied to one or more attachment members (1506), attachment members may pull plates (1508) toward each other. This may, in turn, compress bellows (1510) between plates (1508), as shown in a top view in FIG. 15C. This compression of bellows (1510) may change the shape of bellows (1510) by decreasing their length, and increasing their height, which may cause support member (1502) to provide support a target tissue. Bellows (1510) may be made of any suitable deformable, biocompatible material as described above. Additionally, support device (1500) may include a cover, as described above, but need not. In some variations, bellows (1510) naturally return to their uncompressed state when a force is no longer being applied to the attachment members (1506). In some variations, support device (1500) has one or more components that may act to return bellows (1510) to their uncompressed states when a force is no longer being applied to the attachment members (1506). In other variations, an additional force or stimulus returns bellows (1510) to their uncompressed state when a force is no longer being applied to the attachment members (1506). In some of these variations, the external environment surrounding the support device (1500) may provide the additional force or stimulus.

While shown in FIGS. 15A-15C as each passing through a one plate (1508) and one bellow (1510) and connecting to another plate (1508) at connection point (1516), attachment members (1506) may connect to support member (1502) in any suitable manner. Indeed, in some variations, attachment members (1506) may attach to one plate (1508) at a connection point (1516), but not pass through either bellows (1510)

or another plate (1508). In other variations, attachment members (1506) may pass through one plate (1508) and attach to another, but may not pass through a bellow (1510).

FIGS. 16A and 16B illustrate another suitable variations of support device (1600) comprising a support member (1602) that comprises one or more deformable components (1604). FIG. 16A shows a perspective of view of support device (1600) including attachment members (1606), plates (1608) and deformable component (1604) comprising flexible sheet (1610). While shown in FIGS. 16A and 16B as having strips of material (1612) and connection members (1614), attachment members (1606) may have any suitable configuration of elements as described above.

Generally, attachment members may be attached to one or more plates (1608) at connection points (1616). When a force is applied to one or more attachment members (1606), attachment members may pull plates (1608) toward each other. This may, in turn, compress flexible sheet (1610) between plates (1608), as shown in a perspective view in FIG. 16B. This compression of flexible sheet (1610) may change the shape of flexible sheet (1610) by causing the flexible sheet to bow out, which may cause support member (1602) to provide support a target tissue. Flexible sheet (1610) may be made of any suitable deformable, biocompatible material as described above. Additionally, support device may include a cover, as described above, but need not. In some variations, flexible sheet (1610) naturally return to its uncompressed state when a force is no longer being applied to the attachment members (1606). In other variations, support device (1500) has one or more components that may act to return flexible sheet (1610) to its uncompressed states when a force is no longer being applied to the attachment members (1606). In still other variations, an additional force or stimulus returns flexible sheet (1610) to its uncompressed state when a force is no longer being applied to the attachment members (1606). In some of these variations, the external environment surrounding the support device (1600) may provide the additional force or stimulus.

Figure 17A:
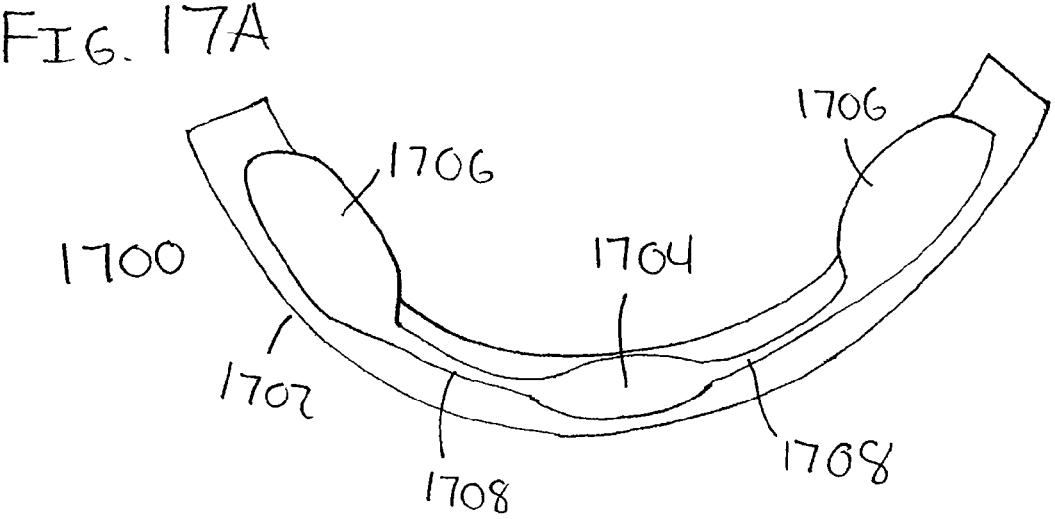
FIGS. 17A and 17B are perspective views of one variation of a support device having a supporting bladder.
Figure 17B:
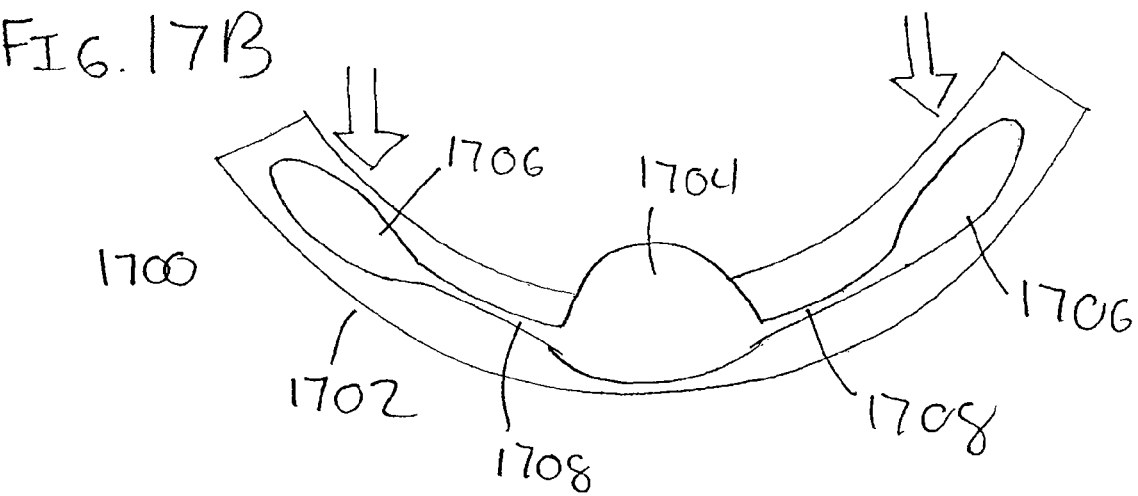

In some variations, the dynamic support device comprises one or more supporting bladders. FIGS. 17A and 17B show one variation of support device (1700) including attachment member (1702), supporting bladder (1704), lateral bladders (1706) and connection channels (1708). In some variations, lateral bladders (1706) may be in fluid communication with supporting bladder (1704). Generally, when a force is applied to the attachment member (1702), the support device (1700) may transfer a fluid from one or more of the lateral bladders (1706) into the supporting bladder (1704). In some variations a force is applied directly to one or more of the lateral bladders (1706), and the one or more lateral bladders (1706) are compressed to drive fluid into the supporting bladder (1704). Transferring fluid into a supporting bladder (1704) may increase the volume of the supporting bladder (1704), and this increase in volume may cause support device (1700) to provide support to a target tissue.

While shown in FIGS. 17A and 17B as having one supporting bladder (1704) and two lateral bladders (1706), support device (1700) may have any number of supporting bladders (1704) and/or lateral bladders (1706). Indeed, support device may have zero, one, or two or more lateral bladders (1706) and may have zero, one, or two or more supporting bladders (1704). In some variations, one or more lateral bladders (1706) may also be used as a supporting bladder (1704). Additionally, while shown in FIGS. 17A and 17B as being semispherical in shape, lateral bladders (1706) and supporting bladders (1704) may have any shape, size, or configuration. Furthermore, lateral bladders (1706) and supporting bladders (1704) may have the same size, shape, or configuration, or may have different sizes, shapes, or configurations.

While shown in FIGS. 17A and 17B as having connection channels (1708), support device (1700) need not. In variations that do include connection channels (1708), the connection channels (1708) may serve as a conduit through which a fluid may be transferred from a lateral bladder (1706) to a supporting bladder (1704), or vice versa. Support device (1700) may comprise any number of connection channels (1708). Indeed, support device (1700) may comprise, zero, one, or two or more connection channels. In some variations, two bladders may be connected with one connection channel (1708). In other variations, two bladders may be connected by two or more connection channels (1708). Furthermore, connection channels (1708) may have any size, shape, or configurations. In some variations, connection channels (1708) may be cylindrical in shape, but need not be. In other variations, connection channels (1708) may be funnel shaped.

Supporting bladder (1704), lateral bladders (1706), and connection channels (1708) may be made from any suitable materials that are capable of enclosing a fluid therein. Examples of suitable materials include, but are not limited, to silicone or any other compliant material described above. Additionally, supporting bladder (1704), lateral bladders (1706), and connection channels (1708) may enclose any suitable fluid, as described above. Support device (1700) may additionally comprise a cover, as described above, but need not.

Support device (1700) may have one or more features to control the passage of fluid between the supporting bladder (1704) and lateral bladders (1706). In some variations, one or more of the bladders may be made from a material that, although deformable, is resistant to deformation. As such, a certain minimum force may be necessary to compress a lateral bladder (1706), thereby ensuring that a fluid is transferred to the supporting bladder (1704) only when sufficient force is applied to the lateral bladder (1704), or vice versa. Similarly, in other variations support device (1700) may include one or more valves (not shown). In some variations, the valves may be configured to allow a fluid to pass therethrough when sufficient pressure is placed against the valve. These valves may require a certain minimum pressure before allowing a fluid to pass therethrough. Additionally, in some variations support device (1700) may include one or more pumps to direct fluid between supporting bladder (1704) and lateral bladders (1706), or vice versa. In some variations, a pump may be used to return the fluid from a supporting bladder (1704) to one or more of the lateral bladders (1706) when a force is no longer being applied thereto. In still other variations, one or more of the bladders may be made from a shape resilient or shape memory material that has a tendency to return to its original shape after being deformed. In some of these variations, one or more lateral bladders (1706) may have a natural tendency to return to an uncompressed state. In these variations, the re-expansion of a lateral bladder (1706) may create a vacuum that draws a fluid from the support bladder (1704).

Any of the dynamic support devices described above may be applied to a number of regions of the human body to provide support to a target bodily tissue. These devices may implanted in any location where providing dynamic support is desirable, including, but not limited to, locations beneath, around, or adjacent to urethral tissue and rectal tissue. In some methods, the device comprises two attachment members at least one support member positioned therebetween, where the at least one support member comprises at least one sliding member and has a first and second configuration, where the application of a first force to one or more of the attachment members slides the at least one sliding member from a first position to a second position, thereby changing the at least one support member from its first configuration to its second configuration. In these methods, the at least one support member may be configured to apply a force to the tissue when the at least one support member is in its second configuration. Additionally, in these methods, the support member may be placed underneath the target tissue.

In other methods, the device comprises first and second attachment members and at least one support member positioned therebetween, where the device has a first configuration and a second configuration, the at least one support member is configured to rotate around an axis of rotation upon application of a first force to one or more of the first and second attachment members, and thereby change the device from its first configuration to its second configuration. In these methods, the at least one support member may apply a force to the tissue when the device is in its second configuration. Additionally, in some of these methods the axis of rotation may be substantially parallel to the direction of the force applied by the at least one support member. In other methods, the axis of rotation may be substantially parallel to the attachment members.

In still other methods, the device comprises first and second attachment members and at least one support member positioned therebetween, where the device has a first configuration and a second configuration, where the at least one support member comprises two or more sections that are configured to rotate around a single pivot point, thereby changing the device from the first configuration to the second configuration, and where the two or more sections compress a target tissue when the device is in its second configuration.

In yet other methods, the device comprises first and second attachment members and at least one support member positioned therebetween, where the at least one support member comprises at least one deformable component, the at least one support member has a first and a second configuration, and the device is configured to compress the at least one deformable component upon application of a first force to one or more of the first and second attachment members, thereby changing the at least one support member from its first configuration to its second configuration. In some of these methods, the support member may be configured to apply a force to a target tissue when the at least one support member is in its second configuration.

In still other variations, the device comprises one or more attachment portions and at least one supporting bladder positioned therebetween, and one or more lateral bladders positioned on the one or more attachment portions in fluid communication with the at least one supporting bladder, where the device is configured to transfer a fluid from the one or more lateral bladders to the at least one supporting bladder upon application of a first force to the one or more attachment portions.

In other variations, the device comprises first and second attachment members and a first plurality of rotating arms positioned therebetween, where the first plurality of rotating arms are configured to rotate in the same direction relative to a first plane upon application of a first force to one or more of the first and second attachment members. In other variations, the device may comprise a second plurality of rotating arms that may rotate in the same direction relative to a second plane upon application of a first force to one or more of the first and second attachment members.

Generally, when any of the above devices are implanted, the attachment members are connected to, attached to, or integrated with bodily tissues. In some methods, one or more of the attachment members are attached to soft tissue. In other methods, one or more of the attachment members are attached to bony structures. The bony structures may be any suitable bony structure, for example, a pelvic bony structure. In still other methods, one attachment member may be attached to soft tissue while the other attachment member may be attached to one or more bony structures.

When any of the above devices are implanted to support urethral tissue, the device may be implanted by any suitable approach and in any suitable fashion. In female patients, the device may be implanted using a transvaginal approach. In male patients, the device may be implanted using a transperineal approach. FIGS. 18A-E show support device (1900) with support member (1902) and attachment members (1904) implanted in different fashions within a female patient having urethra (1906), vagina (1908), retropubic space (1910), pubic synthesis (1912), prepubic space (1914), and rectus fascia (1916). It is important to note that while shown in FIGS. 18A-E as a support device (1900) with support member (1902) and attachment members (1904), any of the devices described above may be implanted in such a fashion.

Figure 18A:
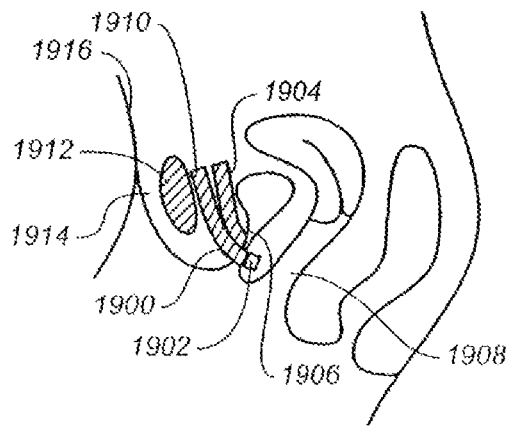
FIGS. 18A-18E are side views of variations of implantation positions for a support device.
Figure 18B:
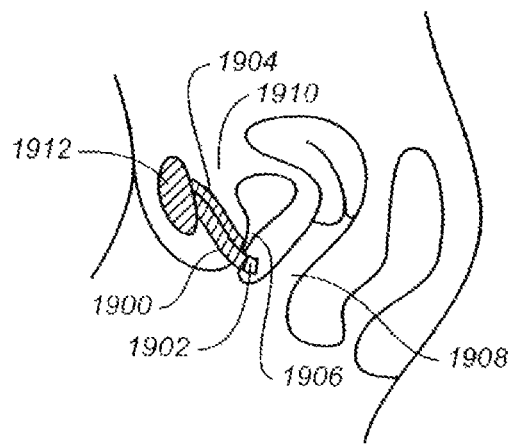

In some methods, implanting the device includes positioning the device such that the support member (1902) is placed beneath the urethra (1906) and above the vagina (1908) and the attachment members (1904) pass through retropubic space (1910). In some of these methods, as shown in FIG. 18A, implanting the device (1900) includes placing the ends of attachment members (1904) within soft tissues located within retropubic space (1910). In other methods, as shown in FIG. 18B, implanting the device (1900) includes attaching the ends of attachment members to pelvic bony structures, such as the pubic synthesis (1912).

To implant support device (1900) beneath the urethra (1906) in one of the above fashions, an incision is first made in the anterior vaginal wall. A surgical tool may then be used to either push or pull one attachment member (1904) into the retropubic space (1910). The attachment member (1904) may then be attached to either soft tissue or the pelvic bony tissues. Once in place, the support member (1902) may be positioned under the urethra (1906), and the other attachment member (1904) may be placed in a similar fashion. In some methods, the attachment members (1904) may be placed simultaneously. Additionally, the device (1900) may be adjusted once put in place. Alternatively, the device (1900) may be retrieved or repositioned if needed.

Figure 18C:
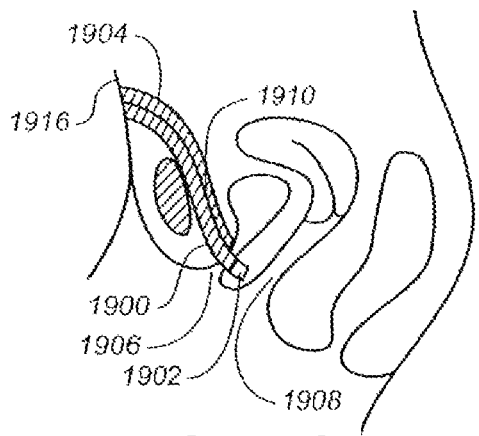

In other methods, the support device (1900) may be implanted such that the ends of attachment members (1904) pass through the retropubic space (1910) and are attached to, or pass through, a patient's rectus fascia (1916), as shown in FIG. 18C. To implant support device (1900) in this configuration, an incision may be made in the anterior vaginal wall of a female patient, and two skin incisions may be made over the rectus fascia (1916). In some methods, support device (1900) may either be pushed or pulled with a surgical device from one skin incision to the anterior vaginal incision, leaving one attachment member (1904) between the two incisions. The support member (1902) may then be positioned beneath the urethra (1906), and the other attachment member (1904) may be either pushed or pulled from the anterior vaginal incision to the second skin incision. Once the device (1900) is in place, it may then be adjusted, removed or repositioned.

In some methods, the device (1900) may be secured to bodily tissue. For example, sutures (not shown) may be used to attach the end of attachment members (1904) to the rectus fascia (1916) or other subdermal tissues. In other methods, sutures may be used to attach the device (1900) to the endopelvic fascia or other periurethral tissues. In methods where the ends of attachment members (1904) are passed outside of the body, these ends may be knotted outside of the body. In others of these methods, the ends of attachment members (1904) may be passed to a different location in the body. In some of these methods, the ends of the attachment members (1904) may be passed to this location through the original skin incisions, and may additionally exit the body through a second set of skin incisions. In others of these methods, the ends of attachment members may re-enter the body through a second set of skin incisions, be passed to a different location in the body, and may additionally exit the body through a third set of skin incisions.

In other methods, the support member (1902) may first be placed beneath the urethra (1906) through the anterior vaginal incision. One attachment member (1904) may then be pushed or pulled from the anterior vaginal incision to a first skin incision, and then the other attachment member (1904) may be pushed or pulled from the anterior vaginal incision to the second skin incision. In still other methods, the device (1900) begins disassembled, and the attachment members (1904) are passed (in either direction) between the skin incisions and the anterior vaginal incision. The support member (1902) may then be placed beneath the urethra, and the device (1900) assembled.

Figure 18D:
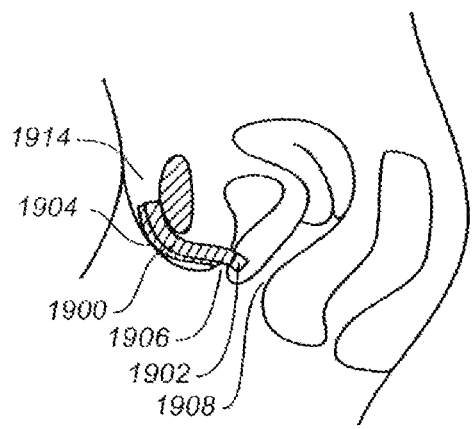
Figure 18E:
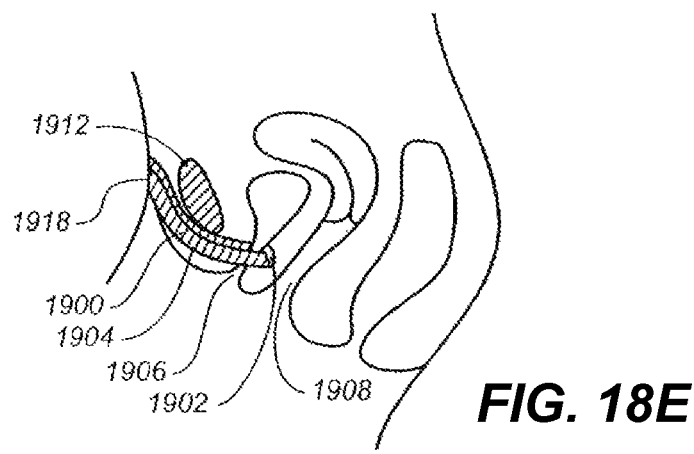

In other methods, implanting the device (1900) includes positioning the device (1900) such that at least a portion of each of the attachment members (1904) is located in the prepubic space (1914). In some of these methods, as shown in FIG. 18D, the ends of the attachment members (1904) may be placed within the prepubic space (1914). The device may be implanted by any of the methods described above, except that the attachment members (1904) will be positioned in the prepubic space (1914). In other methods, as shown in FIG. 18E, the ends of attachment members (1904) may pass through the prepubic space (1914) and may be attached to, or pass through the fascia (1918) located over the pubic synthesis (1912). The device (1900) may be implanted in this configuration by methods similar to those described above, except that the skin incisions may be made in the skin sitting over the pubic synthesis (1912).

In some methods, the device (1900) may be implanted in any of the above fashions without making skin incisions. In these methods, ends of attachment members (1904) may be tunneled to their final placement site. In these methods, attachment members comprising flaring flaps, prongs, hooks, or other anchoring components as described above, may be especially useful in maintaining positioning of the device (1900) within the body.

Figure 19A:
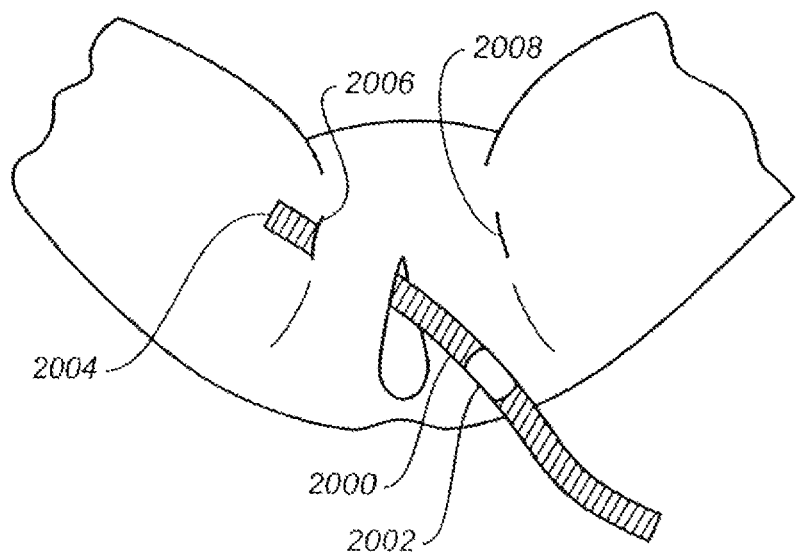
FIGS. 19A and 19B are depictions of a method by which a support device may be implanted using a transobturator approach.
Figure 19B:
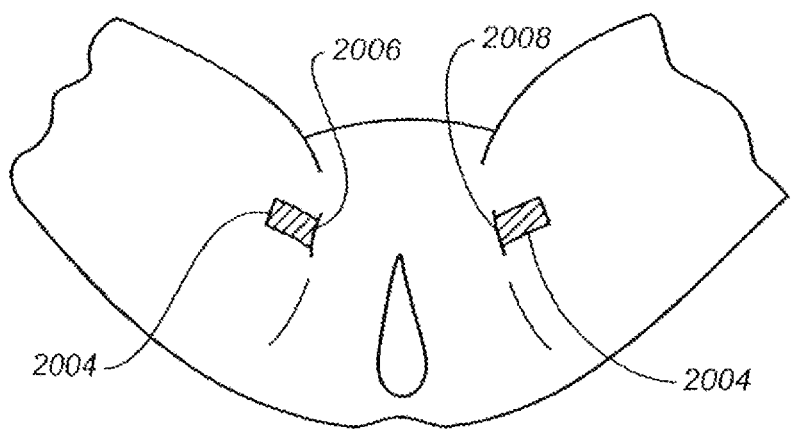

FIGS. 19A and 19B illustrate one method by which device (2000) may be implanted in a patient using a transobturator approach. While FIGS. 19A and 19B show device (2000) as having support member (2002) and attachment members (2004), any of the devices described above may be implanted using this method. In these methods, an incision (not shown) may be made in the anterior vaginal wall of a female patient (or the perineum of a male patient), and first (2006) and second (2008) incisions may be made in the skin over the obturator foramen. In some methods, as shown in FIG. 19A, a surgical device (not shown) may be used to either push or pull one of the attachment members (2004) from the anterior vaginal incision through a first obturator foramen (not shown) to the first skin incision (2006). The support member (2002) may then be placed underneath the urethra (not shown), and the other attachment member (2004) may either be pushed or pulled from the anterior vaginal incision through a second obturator foramen (not shown) to the second skin incision (2008), as shown in FIG. 19B. At this point, the device (2000) may be adjusted, removed or repositioned. In some methods, the ends of the attachment members (2004) may be cut off at the surface of the skin. In some of these methods, the attachment members (2004) are tied to the subdermal soft tissues using sutures. In other methods, the ends of attachment members (2004) may be knotted at the surface of the skin. In yet other methods, sutures may be used to attach the device to the endopelvic fascia or other periurethral, or pelvic tissues. In some methods, the central portion of the device may be anchored to the anterior vaginal wall and other periurethral tissues (in male patients, the central portion may be anchored to the bulbospongiousus muscle or other periurethral tissues). In still other methods, the ends of attachment members (2004) may be passed to a different location in the body, as described above.

In other methods, the device (2000) may be pushed or pulled to the anterior vaginal incision through a first obturator foramen from the first skin incision (2006), leaving one attachment member (2004) between the two incisions. The support member (2002) may then be placed underneath the urethra (not shown), and the other attachment member (2004) may either be pushed or pulled from the anterior vaginal incision through a second obturator foramen (not shown) to the second skin incision (2008), as shown in FIG. 19B. At this point, the device (2000) may be adjusted, removed or repositioned. Alternatively, the device (2000) may begin disassembled, and the attachment members (2004) may be either pushed or pulled (in either direction) through the first and second obturator foramen between the anterior vaginal incision and the first (2006) and second (2008) skin incisions respectively. The support member (2002) may then be placed underneath the urethra, and the device (2000) may then be assembled and adjusted. In other methods, the device may be implanted in a similar fashion without making first (2006) and second (2008) skin incisions, and instead tunneling attachment members (2004) to their respective positions.

Figure 20A:
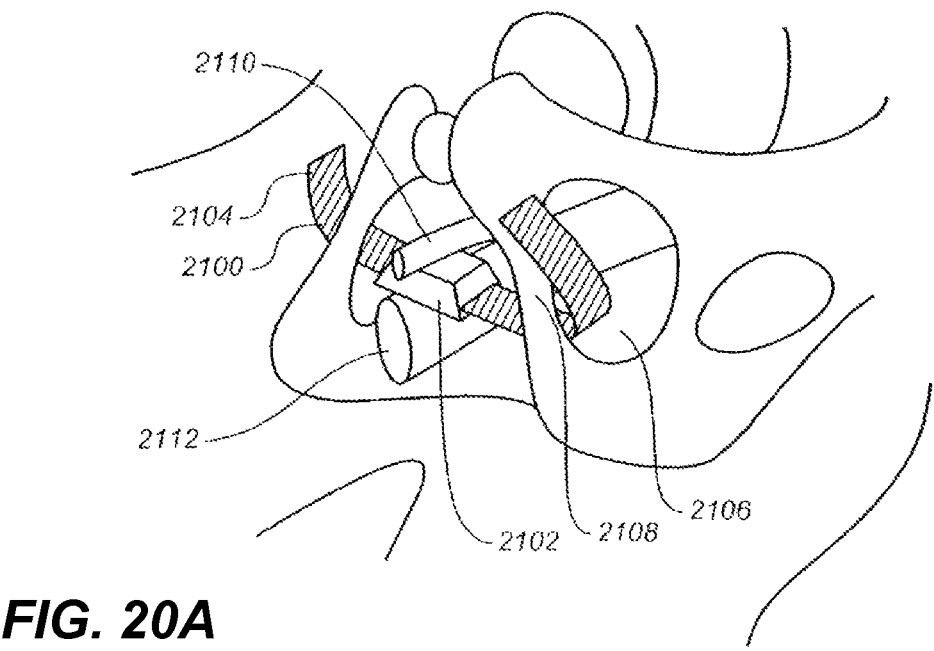
FIGS. 20A and 20B are perspective views of implantation positions for a support device.
Figure 20B:
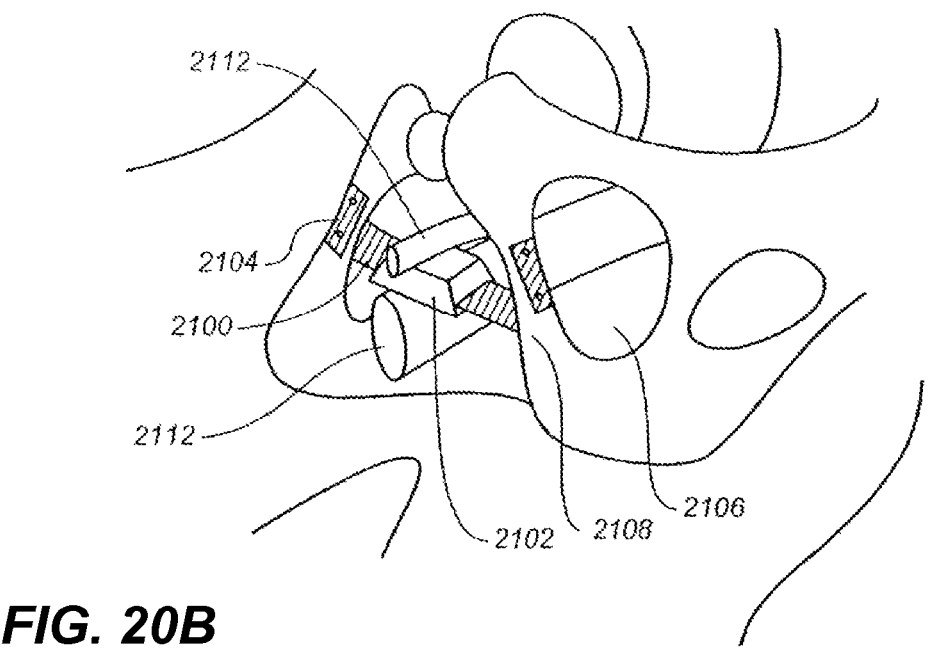

FIGS. 20A and 20B show perspective views of support device (2100) with support member (2102) and attachment members (2104) implanted in a female patient having obturator foramen (2106), descending pubic rami (2108), urethra (2110) and vagina (2112). Although shown in FIGS. 20A and 20B as having support member (2102) and attachment members (2104), the device (2100) may be any of the devices as described above. As shown in FIG. 21A, support member (2102) may be placed between urethra (2110) and vagina (2112), and the attachment members (2104) may pass through the obturator foramen (2106) and be attached to tissue (not shown) within or external to the obturator foramen (2106). Alternatively, as shown in FIG. 20B, the attachment members (2104) may be attached to the descending pubic rami (2108).

Any of the devices described above may also be implanted in male patients. These devices may be implanted using methods similar to those described above for female patients. Instead of the anterior vaginal wall incision made in female patients, a midline incision may be made in the perineum of male patients. This incision may be located between the scrotum and the anus, and may be between about 2 and about 5 cm in length. Dissection may then be carried down through the subcutaneous tissue to the bulbo-spongiosus muscle, which overlays the urethra. In some methods, the device may be placed external to the bulbo-spongiosus muscle. In other methods, dissection may be carried through the bulbo-spongiosus muscle, and the device may be placed internal to the bulbo-spongiosus muscle. In these methods, the device may be placed anywhere along the length of the urethra. In some methods, the device may be placed in a way to proximally relocate the urethra.

In addition, any of the devices described above may alternatively be placed above the urethra, between the urethra and the pubic symphysis. For devices placed in this manner, the attachment members may be placed in any fashion as described above.

While described above as being used to treat urinary incontinence, it should be understood that the devices described here may have broad applications in different portions of the body in order to aid in the treatment of a number of conditions. For example, the devices described here may be used to treat fecal incontinence. In treating fecal incontinence, the central portion of the device may be placed in contact with tissue at or near the anus, above and/or below the levator ani muscles. In some methods, the central portion of the device is placed between the interior and exterior sphincter muscles of the anus. In some methods, the central portion of the device may be placed externally to the exterior sphincter muscles. The attachment members may be placed in any of the configurations as described above in relation to supporting urethral tissue. For example, the ends of the attachment members may be placed in the retropubic space, the prepubic space, may be attached to the rectus fascia, may wrap around bony structures, may be attached external to or within the obturator foramen, or may be attached to a pubic bony structure. In addition the attachment members may be wrapped around the anus and attached to themselves.

The devices described here may be implanted to support rectal tissue using any suitable method. In some methods, an initial incision may be made between the anus and the vagina (or scrotum in male patients). In other methods, an initial incision may be made between the anus and the coccyx. In other methods the device may be implanted through a lower abdominal incision. Dissection may be carried out as necessary to place the central portion of the device. In some methods, the attachment members are passed between this initial incision and skin incisions. In other methods, the attachment members are tunneled from the initial incision to a location within the body. Once placed, the device may be removed, replaced, secured or adjusted.

Also described here are kits. These kits may comprise any suitable components. For example, the kits may comprise one or more of the support devices described above, with or without additional tools (e.g., tools for implantation). The kits may also comprise instructions for using any of the kit components, or for assembling any of the kit components. In some variations, the kit includes a fully-assembled device. In other variations, the kit includes separate, unassembled components of the device. In some of these variations, the kit may also include tools to help with assembly of the device. In others of these variations, the kit may include unassembled components of different sizes or materials.

In variations where the kit comprises a device that is responsive to a stimulus, the kit may additionally include a device for providing a stimulus to the device. For example, in variations in which the device contains a circuit that provides electro-resistive heating, the kit may include a wand or other device that is capable of inducing a current into that circuit. Alternatively, if the device responds to magnetic energy, the kit may include a device that creates a magnetic field.

As noted above, the kits may also comprise tools or other materials to assist in the implantation of the device within a patient. For example, the kit may include one or more scalpels, or other cutting devices for making skin incisions. The kit may also include needles, introducers, alignment tools or guides for passing portions of the device through the body. These kits may also comprise handles, or other devices that may aid in the use and manipulation of the needles, introducers, alignment tools or guides. Furthermore, the kit may include sutures or other anchors to help affix the device within the body.

We claim:

1. A device for supporting a target tissue, comprising:
   first and second attachment members and a support member positioned therebetween, the support member comprising first and second elevated sections;
   wherein the device has a first configuration and a second configuration;
   wherein the support member is configured to rotate around a single axis of rotation upon application of a first tensile force to one or more of the first and second attachment members, and thereby change the device from its first configuration to its second configuration;
   wherein one or more of the first and second elevated sections of the support member are configured to reside under the target tissue in the second configuration and wherein the first and second elevated sections of the support member are configured to reside on either side of the target tissue in the first configuration;
   wherein the support member is configured to apply a compressive force to the target tissue when the device is in its second configuration; and
   wherein the direction of the compressive force is substantially parallel to the axis of rotation.

\* \* \* \* \*